United States Patent [19]

Balkovec et al.

[11] Patent Number: 6,136,853
[45] Date of Patent: Oct. 24, 2000

[54] SORDARIN DERIVATIVES

[75] Inventors: James M. Balkovec, North Plainfield; Bruno Tse, Edison, both of N.J.

[73] Assignee: Merck & Co., Inc., Rahway, N.J.

[21] Appl. No.: 09/284,123

[22] PCT Filed: Oct. 3, 1997

[86] PCT No.: PCT/US97/18047

§ 371 Date: Mar. 6, 1999

§ 102(e) Date: Mar. 6, 1999

[87] PCT Pub. No.: WO98/15178

PCT Pub. Date: Apr. 16, 1998

[51] Int. Cl.$^7$ ................................................ A01N 37/34
[52] U.S. Cl. .................... 514/529; 562/508; 514/460; 549/418; 549/420; 549/475
[58] Field of Search ........................ 549/418, 420, 549/475, 79; 514/460, 311, 378, 277, 438, 347, 533, 529; 546/174, 342; 548/562, 247; 562/508

[56] References Cited

FOREIGN PATENT DOCUMENTS

| 62-040292 | 2/1987 | Japan . |
| 06157582 | 6/1994 | Japan . |
| 1162027 | 8/1969 | United Kingdom . |
| WO96/14326 | 5/1996 | WIPO . |
| WO96/14327 | 5/1996 | WIPO . |

OTHER PUBLICATIONS von D. Hauser, et al., Helvetica Chimica Acta, 54:119–20, (1971).
S. J. Coval, et al., J. Antibiotics, 48:1171–1172, (1995).
N. Kato, et al., J. Chem. Soc., Chem. Commun., 002–1004, (1993).
L. N. Mander, et al., J. Org. Chem. 56(11):3595–3601, (1991).
M. Dawson, et al., Chem. Abstr., vol. 125, No. 1996:479150 (1996).
M. Hayes, et al., Chem. Abstr., vol. 125, No. 1996:455761 (1996).
Patent Abstracts of Japan, vol. 11, No. 229 (C–436) Jul. 25, 1987.
Kato et al "Total Synthesis of Optically Active Sordaricin Methyl Ester and Its Delta 2–Derivative" CA 120:107383 (1993).
Mander et al "Studies on the Synthesis of the Diterpenoid Mold Metabolite Sordaricin . . . " CA 114:229179 1991.

*Primary Examiner*—Amelia Owens
*Attorney, Agent, or Firm*—Shu M. Lee; David L. Rose

[57] ABSTRACT

PURPOSE: To produce a novel antibiotic substance zofimarin having antimicrobial activity against fungi and obtain an antimicrobial agent containing the antibiotic substance zofimarin as an active constituent, by cultivating a microorganism, belonging to the genus Zopfiella and capable of producing the zofimarin.

CONSTITUTION: An ascomycete belonging to the genus Zopfiella, e.g. *Zopfiella marina*; is cultivated. The cultivation is carried out according to general fungi, but artifical seawater is used in place of tap water in a liquid culture medium. A carbon source, nitrogen source, inorganic salt, etc., are added, and a defoaming agent is suitably used to carry out the cultivation at 20–30° C. by the spinner culture method with aeration. After completing the cultivation, microbial cells are removed, and the resultant product in the supernatant liquid or filtrate is extracted and purified to afford the aimed zofimarin. The above-mentioned antibiotic substance is neutral colorless oily substance exhibiting the following properties; Soluble in methanol, ethanol and acetone and slightly soluble in water. Positive to the color reaction with iodine and sulfuric acid, etc., and expressed by the formula.

15 Claims, No Drawings

SORDARIN DERIVATIVES

SUMMARY OF THE INVENTION

The present invention relates to sordarin derivatives which are potent antifungal agents with a broad spectrum of activity, to processes for their preparation, to pharmaceutical and agricultural compositions containing the compounds, and to methods of controlling fungal infections in human, animals and plant materials using such compounds.

BACKGROUND OF THE INVENTION

Sordarin is an antifungal antibiotic isolated from the mould *Sordaria araneosa* (see GB 1,162,027 and *Helvetica Chimica Acta,* 1971, 51:119–20). Other compounds having the sordarin skeleton have also been reported as antifungal agents. Japanese Kokai J62040292 discloses the compound zofimarin isolated from *Zofiela marina* sp.; Japanese Kokai J06157582 discloses the compound BE-31405 isolated from Penicillium sp.; and SCH57404 is reported in *J. Antibiotics,* 1995, 48:1171–1172. Semi-synthetic sordarin derivatives are reported in PCT Applications WO96/14326 and WO96/14327.

Sordaricin, the aglycon, may be obtained from sordarin by acid hydrolysis (Hauser and Sigg, *Helvetica Chimica Acta,* 1971, 51:119–20); similarly sordaricin methyl ester is obtained from sordarin methyl ester. The total synthesis of sordaricin methyl ester is reported in Kato et al, *J. Chem. Soc., Chem. Commun.,* 1993, 1002–1004, which also discloses O-methoxymethyl sordaricin methyl ester. The diacetate of 4-desformyl-4-hydroxymethyl sordaricin is disclosed in Mander and Robinson, *J. Org. Chem.,* 1991, 56(11):3395–3601. Neither sordaricin nor the reported derivatives thereof has been shown to have biological activity.

DETAILED DESCRIPTION OF THE INVENTION

The present invention provides compounds having the formula I:

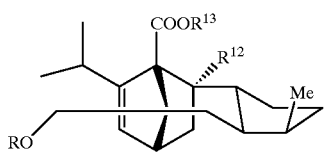

I wherein

R is
(a) $C(=O)OR^1$,
(b) $C(=O)NR^2R^3$,
(c) $C(=O)R^4$,
(d) $CH(R^2)OR^5$,
(e) $C(R^6)(R^7)(R^8)$, (f)

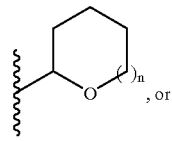

, or (g)

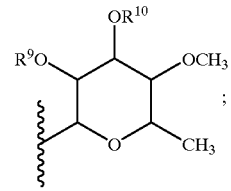

;

with the proviso that when $R^{12}$ is CHO, R is not (g);

$R^1$ is
(a) $C_1-C_{14}$ alkyl,
(b) $C_2-C_{14}$ alkenyl,
(c) $C_2-C_{14}$ alkynyl,
(d) $C_3-C_{20}$ cycloalkyl,
(e) $C_3-C_{20}$ cycloalkenyl,
(f) aryl or
(g) aryl $C_{1-6}$ alkyl;

$R^2$ and $R^3$ are independently
(a) H or
(b) $R^1$;

$R^4$ is
(a) H,
(b) $R^1$ or
(c) $-(CH_2)_m NR^2R^3$;

$R^5$ is
(a) $R^1$ or
(b) $-(CH_2)_x O(CH_2)_y H$;

$R^6$ is
(a) H,
(b) $R^1$,
(c) $-(CH_2)_y CHR_{11}(CH_2)_z H$,
(d) $-(CH_2)_y C \equiv C(CH_2)_z H$,
(e) $-(CH_2)_y C(R^7) = CH(CH_2)_z H$,
(f) $-(CH_2)_y C \equiv C(CH_2)_m R^{11}$,
(g) $-(CH_2)_y C(R^7) = CH(CH_2)_m R^{11}$, $R^7$ and $R^8$ are independently
(a) H, or
(b) $C_1-C_{14}$ alkyl;

$R^9$ and $R^{10}$ are independently
(a) H,
(a) $C_1-C_{14}$ alkyl,
(a) $C_2-C_{14}$ alkenyl,
(a) aryl $C_{1-6}$ alkyl;

$R^{11}$ is
(a) $OR^7$,
(b) $OCH_2CH_2(CH_2)_n OR^7$, or
(c) $NR^2R^3$;

$R^{12}$ is
(a) $-C(=O)R^{14}$,
(b) $-CH=NOH$, or
(c) $-CH_2OCH_3$;

$R^{13}$ is
(a) H,
(b) $-CH_2C_6H_5$,
(c) $-CH_2CH=CH_2$, (d)

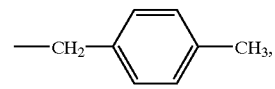

(e) 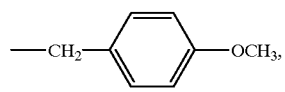

(f) 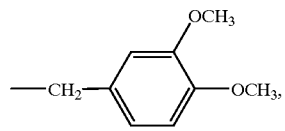

(g) 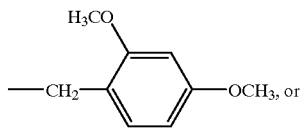

(h) 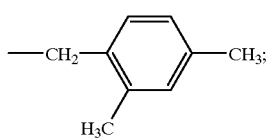

$R^{14}$ is
  (a) H,
  (b) $C_1$–$C_4$ alkyl,
  (c) —$CCl_3$,
  (d) —$CBr_3$,
  (e) —$CF_3$, or
  (f) OH;
n is 0 or 1;
m is 1–6;
x is 2–6;
y is 0–6;
z is 0–6 or
a pharmaceutically or agriculturally acceptable salt thereof.

One embodiment of the present invention provides compounds of formula I wherein
$R^{12}$ is —CHO;
R is
  (a) C(=O)$OR^1$,
  (b) C(=O)$NR^2R^3$,
  (c) C(=O)$R^4$,
  (d) $CH_2OR^5$,
  (e) C($R^6$)($R^7$)($R^8$), (f) 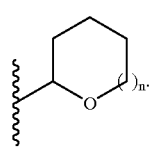

Another embodiment of the present invention provides compounds of formula I wherein
$R^{12}$ is —CHO
$R^{13}$ is H,
R is C(=O)$OR^1$.

Another embodiment of the present invention provides compounds of formula I wherein
$R^{12}$ is —CHO $R^{13}$ is H,
R is C(=O)$NR^2R^3$.

Another embodiment of the present invention provides compounds of formula I wherein
$R^{12}$ is —CHO
$R^{13}$ is H,
R is C(=O)$R^4$.

Another embodiment of the present invention provides compounds of formula I wherein
$R^{12}$ is —CHO
$R^{13}$is H,
R is C($R^2$)$OR^5$.

Another embodiment of the present invention provides compounds of formula I wherein
$R^{12}$ is —CHO
$R^{13}$ is H,
R is C($R^6$)$R^7$)$R^8$).

Another embodiment of the present invention provides compounds of formula I wherein
$R^{12}$ is —CHO
$R^{13}$is H;

R is 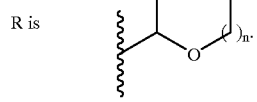

A preferred embodiment of the present invention provides compounds of formula I wherein
$R^{12}$ is —CHO,
$R^{13}$ is H,
R is CH($R^6$)($R^7$),
$R^6$ is
  (a) H,
  (b) $R^1$
  (c) —$(CH_2)_y$$CHR^{11}$$(CH_2)_z$H,
  (d) —$(CH_2)_y$C($R^7$)=CH$(CH_2)_z$H,
$R^7$ is H or $C_1$–$C_6$ alkyl,
$R^{11}$ is $OR^7$.

Another preferred embodiment of the present invention provides compounds of formula I wherein
$R^{12}$ is —CHO
$R^{13}$is H,
R is
  (a) —$CH_3$,
  (b) —$CH_2CH_3$,
  (c) —$CH_2CH_2CH_3$,
  (d) —$CH_2CH_2CH_2CH_3$,
  (e) —$CH_2CH_2CH_2CH_2CH_3$,
  (f) —$CH_2CH_2CH_2CH_2CH_2CH_3$,
  (g) $CH_2CH_2CH_2CH_2CH_2CH_2CH_3$,
  (h) —CH$(CH_3)_2$,
  (i) —$CH_2CH(CH_3)_2$,
  (j) —$CH_2CH_2CH(CH_3)_2$,
  (k) —$CH_2C_6H_5$,
  (l) —$CH_2$CH=$CHCH_3$,
  (m) —$CH_2$CH=CH$CH_2CH_3$,
  (n) —$CH_2$CH=CH$CH_2CH_2CH_3$,
  (o) —$CH_2$CH=CH$CH_2CH_2CH_2CH_3$ A more preferred embodiment of the present invention provides compounds of formula I wherein R¹² is —CHO
R¹³ is (a) H,
R is
(a) —CH₂CH₂CH₃,
(b) —CH₂CH₂CH₂CH₃,
(c) —CH₂CH₂CH₂CH₂CH₃,
(d) —CH₂CH(CH₃)₂,
(e) —CH₂CH₂CH(CH₃)₂,
(f) (Z)—CH₂CH═CHCH₂CH₃,
(g) (Z)—CH₂CH═CHCH₂CH₂CH₃.

In another aspect of the present invention, there is provided a pharmaceutical composition which comprises an antifungal effective amount of a compound of formula I, and a pharmaceutically acceptable carrier. Also provided is a pharmaceutical composition which is made by combining a compound of formula I and a pharmaceutically acceptable carrier.

Another aspect of the present invention provides an agricultural composition which comprises an antifungal effective amount of a compound of formula I, and an agriculturally acceptable carrier thereof. Also provided is an agricultural composition which is made by combining a compound of formula I and an agriculturally acceptable carrier.

Yet another aspect of the present invention provides a method for treating fungal infection in an animal (including humans) which comprises administering to an animal in need of such treatment an antifungal effective amount of a compound of formula I.

A further aspect of the present invention provides a method for controlling phytopathogenic fungi in plants which comprises applying to said plant an antifungal effective amount of a compound of formula I.

As used herein, unless otherwise specified, the following terms have the indicated meanings.

The term "alkyl", alone or as part of a group (e.g. aralkyl), means a straight or branched chain alkyl moiety, optionally substituted with cycloalkyl or cycloalkenyl, having the designated number of carbon atoms such as methyl, ethyl, n-propyl, n-butyl, isopropyl, isobutyl, isopentyl, s-butyl, t-butyl, n-hexyl, n-octyl, decyl, undecyl, cyclopropylmethyl, cyclobutylmethyl, 2-cyclopentylethyl, cyclododecylmethyl, cyclohexylmethyl and the like.

The term "cycloalkyl" means a saturated carbocycle containing one or more rings of from 3 to 12 carbon atoms, optionally substituted with C₁₋₃ alkyl. Examples of cycloalkyl groups are cyclopropyl, cyclobutyl, cyclopentyl, cyclohexyl, methylcyclohexyl, cycloheptyl, adamantyl, 2-ethyl-1-bicyclo[4.4.0]decyl, and the like.

The term "aryl", alone or as part of a group (e.g. aralkyl), includes phenyl, biphenyl, terphenyl, naphthyl, anthracenyl or heteroaryl each optionally substituted by one to three groups independently selected from halogen, hydroxyl, carboxyl, C₁₋₆ alkyl, C₁₋₆ alkoxy or C₁₋₄ alkoxycarbonyl. The heteroaryl group may be a 5- or 6-membered heteroaromatic ring containing one or more heteroatoms selected from nitrogen, oxygen and sulfur. Suitable examples of heteroaryl groups include pyridyl, quinolinyl, furyl, thienyl and pyrrolyl.

The term "alkenyl" means a straight or branched carbon chain having at least one carbon-carbon double bond. Examples include vinyl, allyl, butenyl, isobutenyl, butadienyl, and the like.

The term "cycloalkenyl" means an unsaturated carbocycle containing one or more rings of from 3 to 12 carbon atoms, optionally substituted with C₁₋₃ alkyl. Examples of cycloalkyl groups are cyclobutenyl, cyclopentenyl, cyclohexenyl, methylcyclohexenyl, and the like.

The term "alkynyl" means a straight or branched carbon chain having at least one carbon-carbon triple bond. Examples include acetylenyl, propargyl, butynyl, 1,3-pentadiynyl, and the like.

The term "controlling", used in association with phytopathogenic fungi, includes prophylactic use (i.e. to protect against infection) and curative use (i.e. to eradicate infection).

The term "plants" include live plants, foliage, flowers, seeds, fruits, and other materials derived from plants. The term also includes roots of the plant via application of the active ingredient to the soil.

The term "composition", as in pharmaceutical or agricultural composition, is intended to encompass a product comprising the active ingredient(s), and the inert ingredient(s) that make up the carrier, as well as any product which results, directly or indirectly, from combination, complexation, aggregation, or other interactions of any two or more of the ingredients, or from dissociation of one or more of the ingredients, or from other types of reactions of one or more of the ingredients.

Suitable salts of a compound of formula I include inorganic base salts such as alkali metal salt (e.g. sodium and potassium salts), ammonium salts, and organic base salts. Suitable organic base salts include amine salts such as tetraalkylammonium (e.g. tetrabutylammonium or trimethylcetylammonium), trialkylamine (e.g. triethylamine), dialkylamine salts (e.g. dicyclohexylamine), optionally substituted benzylamine (e.g. phenylbenzylamine or p-bromobenzylamine), ethanolamine, diethanolamine, N-methylglucosamine, N-methylpiperidine, pyridine and substituted pyridine (e.g. collidine, lutidine, 4-dimethylaminopyridine), and tri(hydroxymethyl) methylamine salts, and amino acid salts (e.g. lysine or arginine salts).

Compounds of formula I are prepared from sordarin (II) or its aglycone, sodaricin. Sordarin is [1R-(1α,3aβ,4β,4aβ, 7β,7aα,8aβ)]8a-[(6-deoxy-O-methyl-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid having the formula II:

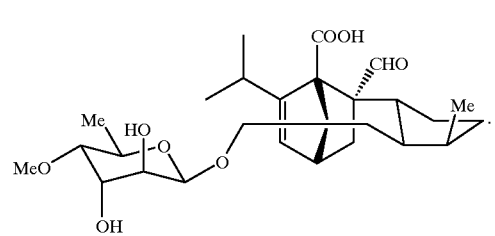

II

Sordarin can be obtained by the cultivation of *Sordaria araneosa* NRRL 3196 (also deposited with the ATCC as ATCC 36386) according to the procedure described in GB1,162,027 or in WO96/14326. Sordarin can also be isolated from the fermentation of *Rosellinia subiculata* (ATCC 74386) or an unidentified fungus (ATCC 74387) as described hereinbelow. Both cultures were deposited on Aug. 27, 1996 in the permanent collection at the American Type Culture Collection, 12301 Parklawn Drive, Rockville, Md. 20852, USA under the terms of The Budapest Treaty on the International Recognition of the Deposit of Microorganisms for the Purposes of Patent Procedure.

Sordaricin (III) is [1R-(1α,3aβ,4β,4aβ,7β,7aα,8aβ)]4-formyl-8a-(hydroxymethyl)-4,4a,5,6,7,7a,8,8a-octahydro-7-methyl-3-(1-methylethyl)-1,4-methano-s-indacene-3a (1H)-carboxylic acid having the formula III:

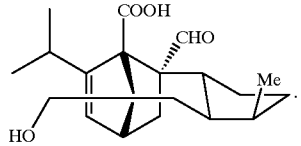

(III)

Sordaricin can be prepared from sordarin by treatment with concentrated hydrochloric acid. As disclosed in WO96/14326 sordaricin is also obtained from fermentation of a mutant derived from *Sordaria araneosa* NRRL 3196, and by biotransformation of sordarin using a Coryneform species.

The compounds of the present invention (formula I) may be prepared by the processes described below. The conditions are representative and are not meant to be limiting.

Scheme 1 shows the conversion of sordarin or a derivative of sordarin to its 4-aldoxime or 4-methoxymethyl derivative. The aldoxime may be prepared by treating the aldehyde compound with hydroxylamine hydrochloride in an alcohol-pyridine solvent system. The methoxymethyl compound may be prepared by first protecting the carboxylic acid group of sordarin or a derivative (such as a benzyl ester for example), followed by reduction of the aldehyde with sodium borohydride in an alcohol solvent. The resultant alcohol is methylated in the presence of a strong base such as sodium hydride with methyl iodide. Removal of the protecting group produces a compound of formula I.

SCHEME 1

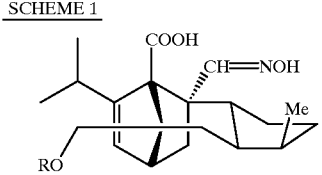

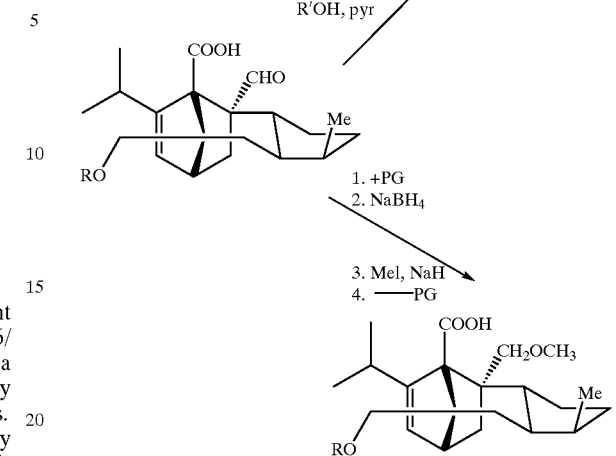

R'OH is a lower alkyl alcohol solvent;
PG is a carboxylic acid protecting group.

Scheme 2 depicts the synthesis of carbamate, ester and carbonate derivatives of sordarin aglycone. The preparation of carbamates may be carried out by treatment of suitably protected sordarin aglycone with an isocyanate (in the examples where $R^3$ is H) or a carbamoyl halide or other activated carbamoylating agent in an inert solvent. Removal of the protecting group produces a carbamate compound of formula I.

Ester derivatives may be prepared in a similar fashion by treatment of protected sordarin aglycone with an activated carbonyl compound such as an acid chloride or mixed anhydride preferably in the presence of an acylation catalyst such as N,N-dimethylaminopyridine and a base such as pyridine. Removal of the protecting proup yields an ester compound of formula I.

Carbonate derivatives may be prepared by the treatment of protected sordarin aglycone with an activated carbonate such as a chloroformate or pyrocarbonate. An acylation catalyst such as N,N-dimethylaminopyridine and a base such as pyuridine is preferably employed in the reaction mixture. Removal of the protecting proup yields a carbonate compound of Formula 1.

SCHEME 2

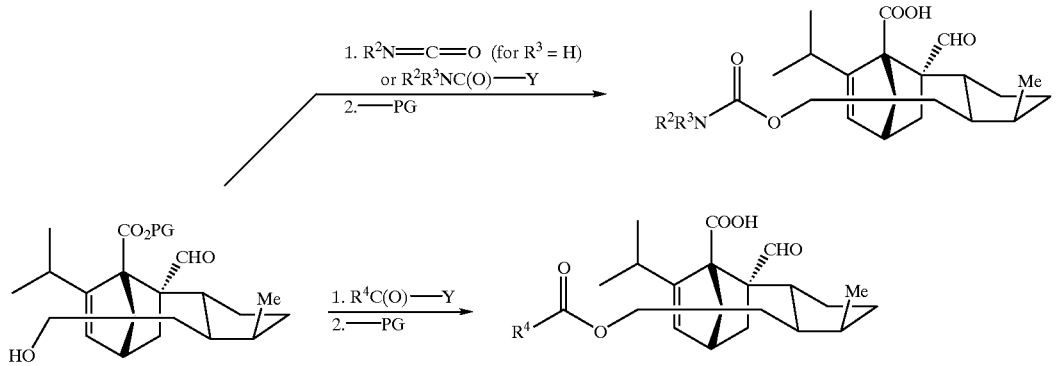

-continued

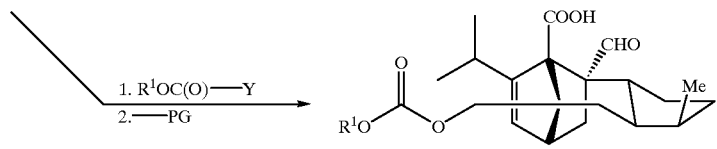

PG is a carboxylic acid protecting group;
C(O)Y is an activated carbonyl such as an acid halide or an anhydride.

Scheme 3 shows the synthesis of ether derivatives of sordarin aglycone. Treatment of the carboxylic acid-protected aglycone with an α-haloether under basic conditions or a vinyl ether under acidic conditions gives rise to the substituted α-alkoxyether derivatives. Treatment of protected sordarin aglycone with a primary or secondary halide or sulfonate and a suitable base such as sodium hydride under $S_N2$ conditions gives the corresponding primary or secondary ether derivatives whereas treatment of the aglycone with a tertiary alcohol, halide or sulfonate and a Lewis acid under $S_N1$ conditions gives the corresponding tertiary ether derivative. Removal of the protecting group from the compound gives a compound of formula I.

The preparation of cyclic acetals from protected sordarin aglycone is depicted in Scheme 4. Treatment of the aglycone with a cyclic vinyl ether in the presence of an acid catalyst followed by removal of the protecting group gives a compound of formula I.

SCHEME 4

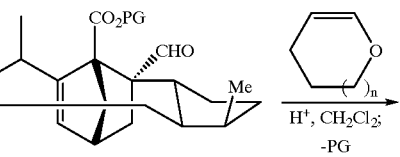

SCHEME 3

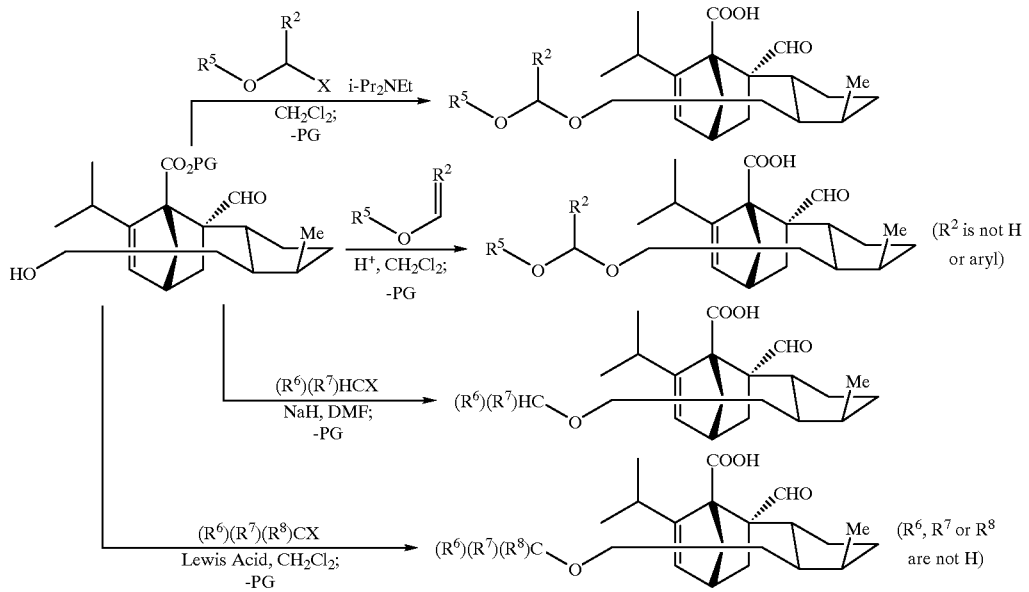

PG is a carboxylic acid protecting group;
X is a conventional leaving group such as halide or sulfonate.

-continued

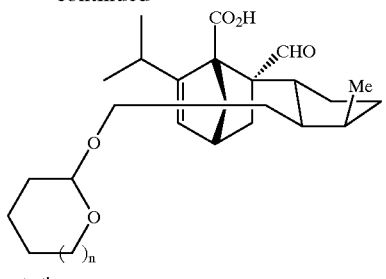

PG is a carboxylic acid protecting group

The preparation of ether derivatives of sordarin where $R^{12}$ is either —CH=NOH or —CH$_2$OCH$_3$ is shown in Scheme 5. Treatment of the protected sordarin derivative with a strong base such as sodium hydride and an alkyl, alkenyl or aralkyl halide or tosylate under conditions that favor an $S_N2$ displacement reaction followed by removal of the protecting group results in a compound of formula I.

SCHEME 5

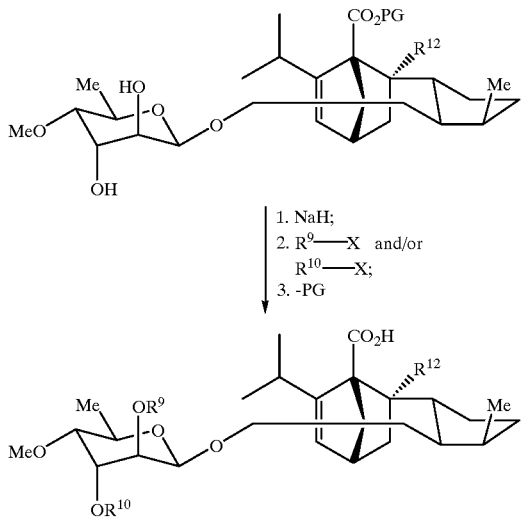

PG is a carboxylic acid protecting group;
X is a conventional leaving group such as halide or sulfonate.

Utility. Compounds of formula I are antifungal agents useful as human and animal medicaments, as well as crop protectants.

The compounds of formula I are very active fungicides useful in combating fungal infections in animals, including humans. For example, they may be used in the treatment of fungal infections caused by organisms such as species of Candida (e.g. *Candida albicans, Candida glabrata, (Torulopsis glabrata), Candida tropicalis,* and *Candida pseudotropicalis*), *Cryptococcus neoformans, Pneumocystis carinii,* Aspergillus Sp (e.g. *Aspergillus flavus* and *Aspergillus fumigatus*), Coccidioides (e.g. *Coccidioides immitis*), Paracoccidioides (e.g. *Paracoccidioides brasiliensis*), Histoplasma (e.g. *Histoplasma capsulatum*) or Blastomyces (e.g. *Blastomyces dennatitidis*). They may also be used to treat other fungal infections caused by species of Trichophyton, Microsporum or Epidermophyton (e.g. *Trichophyton mentographytes, Trichophyton rubrum, Microsporum canis* or *Epidernophyton floccosum*), or in mucosal infections caused by *Candida albicans*.

Compounds of formula I may also be used to treat other infections caused by species of filamentous fungi such as Geotrichum (e.g. *Geotrichum clavatum*), Trichosporon (e.g. *Trichosporon beigelii*), Blastoschizomyces (e.g. *Blastoschizomyces capitatus*), Sporothrix (e.g. *Sporothrix schenckii*), Scedosporium (e.g. *Scedosporium apiosperum*), Cladosporium (e.g. *Cladosporium carrionii*) and *Pityrosporum ovale*.

The compounds of formula I may also be used to treat infections caused by protozoa such as Toxoplasma, Cryptosporidium, Leishmania, Tripanosoma, Giardia and Trichomonas.

The in vitro evaluation of the anti-fungal activity of compounds of the invention was performed on liquid or solid medium by the anti-fungal two-fold serial dilution technique of determining the minimum inhibitory concentration (MIC) of anti-fungal agent that inhibited development of growth after 24 to 48 hours of incubation at 35° C. In practice, a series of agar plates or broth microdilution panels containing two-fold dilutions of anti-fungal agent tested were inoculated with a standard culture of a clinically relevant pathogen, for example, *Candida albicans*. The agar plates or broth microdilution panels were then examined for the presence or absence of growth of the fungus and the appropriate MIC values were noted. Visualization of endpoints was assisted by employment of the vital stain Alamar Blue.

The in vivo evaluation of compounds of formula I can be carried out at a series of dose levels by administration (e.g. subcutaneously, orally, intraperitoneally or intravenously) to mice inoculated intravenously with a strain of Candida spp. The kidneys of the test animals may be removed and quantitated for viable Candida spp. and the reduction in infection may be determined relative to untreated control animals.

In view of their antifungal activity, compounds of formula I are useful for the treatment and/or prevention of a variety of fungal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal diaper rash, candida vulvitis, candida balanitis and otitis extema. They may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

Compounds of formula I also have use as broad spectrum crop antifungal agents and are effective on a broad spectrum of phytopathogenic fungi, in particular those from the class consisting of: Deuteromycetes (e.g. Botrytis spp., Septoria spp., Pyricularia spp., Stagnospora spp., Helminthosporium spp., Fusarium spp., Cercospora spp., Rhynchosporium, spp. Pseudocercosporella, spp. and Alternaria spp.); Basidiomycetes (e.g. Puccinia spp., Rhizoctonia spp., and Hemileia); Ascomycetes (e.g. Venturia spp., Podospharera spp., Erysiphe spp., Monilinia spp. and Uncinula spp.); and Oomycetes (e.g. Phytophthora spp., Pemospora spp., Bremia spp., Pythium spp., and Plasmopara spp.). The foregoing list exemplifies the phytopathogenic fungi against which the named compounds demonstrate activity, and is not limiting in any manner. These compounds have very advantageous curative and preventive fungicidal properties for protecting plants, and can be used to inhibit or to destroy the microorganisms occurring on plants or on parts of plants (the fruit, blossom, leaves, stalks, tubers or roots) of different crops of useful plants, while at the same time parts of plants that grow later are also protected against such microorganisms. They can also be used as dressings in the treatment of plant propagation material, especially seed (fruit, tubers, grain) and plant cuttings (for example rice), to provide protection against fungal infections and against phytopathogenic fungi occurring in the soil. Compounds of formula I of the invention are distinguished by the fact that they are especially well tolerated by plants and are environmentally friendly.

Agricultural evaluation of compounds of formula I can be carried out using the following tests.

1. Action Against *Erysiphe graminis* on Wheat a) After 1 week cultivation, wheat plants are sprayed to run off with a spray mixture (200 ppm active ingredient/20% acetone/0.25% Triton X155). After 2 hours, the treated plants are infected with ascospores shaken from inoculum plants. Fungal attack is evaluated after incubation for 8 days at 22° C. at 50% relative humidity to determine the protection given by the compound.

b) After 1 weeks cultivation, wheat plants are infected with ascospores shaken from inoculum plants. After 24 hours, the wheat plants are sprayed with a spray mixture (200 ppm active ingredient/20% acetone/0.25% Triton X155). Fungal attack is evaluated after incubation for 8 days at 22° C. at 50% relative humidity to determine the degree of curative activity provided by the compound.

c) After 1 weeks cultivation, wheat plants are infected with ascospores shaken from inoculum plants. After 24 hours, the soil in which the wheat plants are growing is drenched with the drench mixture (200 ppm active ingredient/20% acetone/0.25% Triton X155). Fungal attack is evaluated after incubation for 8 days at 22° C. at 50% relative humidity to determine the degree of curative activity provided by the compound.

2. Action Against *Puccinia recondita* on Wheat a) After 1 weeks cultivation, wheat plants sprayed to run off with a spray mixture (200 ppm active ingredient/20% acetone/0.25% Triton X155). After 2 hours, the treated plants are infected with a spore. Fungal attack is evaluated after incubation for 1 day at 95–100% relative humidity at 20° C. followed by 7 days at 25° C. at 50% relative humidity to determine the protection given by the compound.

b) After 1 weeks cultivation, wheat plants are infected with a spore suspension After 24 hours, the infected plants are sprayed to run off with a spray mixture (200 ppm active ingredient/20% acetone/ 0.25% Triton X155. Fungal attack is evaluated after incubation for 1 day at 95–100% relative humidity at 20° C. followed by 7 days at 25° C. at 50% relative humidity to determine the degree of curative activity provided by the compound.

c). After 1 weeks cultivation, wheat plants are infected with a spore suspension After 24 hours, the soil in which the wheat plants are growing was drenched with the drench mixture (200 ppm active ingredient/20% acetone/0.25% Triton X155). Fungal attack is evaluated after incubation for 1 day at 95–100% relative humidity at 20° C. followed by 7 days at 25° C. at 50% relative humidity to determine the degree of curative activity provided by the compound.

Based on the spectrum of activity, the compounds of the present invention can be used to protect or cure plants of phytopathogenic fungi affecting various useful crops. The following species of plants are suitable for the use described in the scope of the invention of the stated compounds: cereal (e.g. wheat, rye, oat, barley, rice, sorghum and related crops); beet (sugar beet and fodder beet); pomes, dropes and soft fruit (e.g. apples, pears, plums, peaches, almonds, cherries, strawberries, raspberries, and blackberries); leguminous plants (e.g. beans, peas, lentils and soybeans); oil plants (rape, mustard, poppy, olives, sunflowers, coconut, castor oil plants, cocoa beans and groundnuts); curbitats (e.g. cucumber, squash, and melon); fiber plants (e.g. cotton, flax, hemp, and jute); citrus fruit (e.g. oranges, lemons, madarins and grapefruit); vegetables (e.g. lettuce, cabbage, spinach, carrot, asparagus, paprika, onions, tomatoes, and potatoes); lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). However, the aforementioned plant species do not constitute a limiting list of plants with respect to spectrum by the stated compounds.

The compounds of formula I are particularly useful for controlling the following plant diseases:

*Erysiphe graminis* in cereals, *Erysiphe cichoracearum* and *Sphaerotheca fuliginea* in cucurbits, *Podosphaera leucotricha* in apples, *Uncinula necator* in vines, Puccinia species in cereals, *Rhizoctonia solani* in cotton, Ustilago species in cereals and sugar cane, *Venturia inaequalis* (scab) in apples, Helminthosporium species in cereals, *Septoria nodorum* in wheat, *Botrytis cinerea* (gray mold) in strawberries and grapes, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in various plants, *Plasmopara viticola* in grapes, Alternaria species in fruit and vegetables. The compounds of formula I may also be used for protecting materials (e.g. preservation of timber against *Paecilomyces variotii*).

Pharmaceutical Compositions. While it is possible that, for use in therapy, compounds of the invention may be administered as the raw chemical, it is preferable to present the active ingredient in a pharmaceutical composition. The invention thus further provides a pharmaceutical composition comprising a compound of formula (I) or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, rectal, topical, ophthalmic or genito-urinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol;

lubricants, for example, magnesium stearate, stearic acid, talc, polyethylene glycol or silica; disintegrants, for example, potato starch or sodium starch glycollate or cross-carmellose sodium; or wetting agents such as sodium lauryl sulphate. The tablets which include chewable, dispersible or effervescent tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilizing and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurized packs with the use of a suitable propellant, e.g. dichlorofluoromethane, trichlorofluoromethane, dichlorotetrafluoroethane, carbon dioxide or other suitable gas, or from a nebuliser. In the case of a pressurized aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilized components. Pour-ons may, for example, be formulated for veterinary use in oils containing organic solvents, optionally with formulatory agents, e.g. stabilizing and solubilizing agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilizing, dispersing and or flavouring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary number of days.

Compounds of the invention may also be used in combination with other therapeutic agents, and the invention thus provides, in a further aspect, a combination comprising a compound of the invention together with another therapeutically active agent.

Thus, for example the compounds of the invention may be used in combination with one or more other antifungal agents, such as a polyenic derivative e.g. (Amphotericin B, Nystatin, a lipid formulation of Amphotericin B) an azole derivative e.g. (Fluconazole, Intraconazole, Ketoconazole, Miconazole, Clotrimazole, ZD-08070, UK-109496, SCH 56592), 5-Fluorocytosine, a Pneumocandin or Echinocandin derivative such as Cilofungin, LY-303366, L-733560, L-743872 or other cell wall active compound such as Nikkomycin Z and/or one or more immunomodulating agents such as an interferon e.g. IFN-), interleukine e.g. (IL-1, IL-2, IL-3 and IL-8) and colony stimulating factors, [(G)-CSF, (M)-CSF and (GM)-CSF] and defensines. Particularly advantageous compounds for use with compounds of the invention include Intraconazole, Flucytosine, Fluconazole or Amphotericin B.

When the compounds of the invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations When a compound of the invention is used in combination with a second therapeutic agent against the same condition the dose of each compound may differ from that when the compound is used alone. Appropriate doses will be readily appreciated by those skilled in the art.

Agrochemical Compositions. The compounds of formula I can be used in either an unmodified form or preferably together with adjuvants conventionally employed in the art of agrochemical formulation and are for this purpose forms known mainly as: emulsifiable concentrates, coatable pastes, directly sprayable or dilutable solutions, dilute solution, suspensions (including high-percentage aqueous, oily or other suspensions), dispersions, oil dispersions, broadcasting agents, wettable powders, soluble powders, dusts, granules, and encapsulations. The formulations are prepared in known manner, e.g. by homogeneously mixing and/or grinding the active ingredients with extenders, e.g. solvents, solid carriers and, where appropriate, surface-active compounds (surfactants). Powders, dusts and broadcasting agents may be prepared by mixing or grinding the active ingredients with a solid carrier. Granules, e.g., coated, impregnated or homogeneous granules, may be prepared by bonding the active ingredients to solid carriers.

Suitable solvents are: aromatic hydrocarbons, preferably the fractions containing 8 to 12 carbon atoms, such as xylene mixtures or substituted naphthalenes, chlorinated aromatics such as chlorobenzenes, phthalates, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones such as cyclohexanone, amines such as ethanolamine, strongly polar solvents, such as N-methyl-2-pyrrolidone, dimethyl sulfoxide or dimethylformamide, and vegetable oils or epoxidised vegetable oils, such as epoxidised coconut oil or soybean oil; and water.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Examples of solid carriers are mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Compounds of formula I may be mixed and applied together with other active ingredients, for example herbicides, insecticides, bactericides, nematocides, molluscicides, growth regulators, micronutrients, and fertilizers. The other ingredients may also be one or more fungicides belonging to but not restricted to the following classes of fungicides: carboxamides, benzimidazoles, triazoles, hydroxypyridines, dicarboximides, phenylamides, thiadiazoles. carbamates, cyano-oximes, cinnamic acid derivatives, morpholines, imidazoles, B-methoxy acrylates and pyridines/pyrimidines. Furthermore, these additional active ingredients may be used as mixtures of several of the preparations, if desired together with other application promoting adjuvants usually used in the art of formulation.

Suitable carriers and adjuvants can be solid or liquid and correspond to the substances typically used in formulation technology (e.g. natural or regenerated mineral substances, solvents, disperants, and wetting agents).

The following list of fungicides with which compounds of formula I may be combined is intended to illustrate possible combinations but not to impose any restrictions. Examples of fungicides which may be combined with compounds of formula I are: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis (thiocarbamyl)disulfide; nitro derivative, such as dinitro(1-methylheptyl)-phenyl crotonate, 2-sec-butyl-4,6-dinitrophenyl 3,3-dimethylacrylate, 2-sec-butyl-4,6dinitrophenyl isopropylcarbonate and diisopropyl 5-nitroisophthalate; heterocyclic substances, such as 2-heptadecylimidazol-2-yl acetate, 2,4-dichloro-6-(o-chloroanilino)-s-triazine, O,O-diethyl phthalimdophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithio[4,5-b] quinoxaline, methyl 1-(butylcarbamyl)-2-benzimidazolecarbamate, 2-methoxycarbonylaminobenzimidazole, 2-(fur-2-yl)-benzimidazole, 2-(thiazol-4-yl)benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1, 2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiyne, 2,3-dihydro-5-carboxanilido-6-methyl-1,4-oxathiyne 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-diethylfuran-3-carboxamide, 2-methylbenzanilide, 2-iodobenzanilide, N-formyl-N-morpholine-2,2,2-trichloroethylacetal, piperazine-1,4-diylbis-(1-(2,2,2-trichloroethyl)-formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N[3-(p-tert.- butylphenyl)-2-methylpropyl]-cis-2,6-dimethylmorpholine, N-3-(p-tert.-butylphenyl)-2-methylpropyl]-piperidine, 1-2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2, 4,6-trichlorophenoxyethyl)-N]-imidazolylurea, 1-(4-chlorophenoxy)-3,3-dimethyl-1-(1H-1,2,4-triazol-1-yl)-butan-2-one, 1-(4-chlorophenoxy)-3,3-dimethyl-1-(1H-1,2, 4-triazol-1-yl)-butan-2-ol, alpha-(2-chlorophenyl)-alpha-(4-chlorophenyl)-5-pyrimidinemethanol, 5-butyl-(2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene, and various fungicides, such as dodecylguanidine acetate, 3-[3-(3,5-dimethyl-2-oxycyclohexyl)-2-hydroxyethyl]-glutaramide, hexachlorobenzene, DL-methyl-N-(2,6-dimethylphehyl)-N-fur-2-yl alanate, methyl DL-N-(2,6-dimethylphenyl)-N-(2]-methoxyacetyl)-alanate, N-(2,6-dimethylphenyl)-N-chloroacetyl-DL-2-aminobutyrolactone, methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2, 4-dichlorophenyl)-pentyl]-1H-1,2,4-triazole, 2,4-difluoro-a-(1H-1,2,4-triazol-1-ylmethyl)-benzhydryl alcohol, N-(3-chloro-2,6-dinitro-4-trifluoromethylphenyl)-5-trifluoromethyl-3-chloro-2-aminopyridine, and 1 -((bis-(4-fluorophenyl)-methylsilyl)-methyl)-1H-1,2,4-triazole.

As with the nature of compositions, the method of application such as spraying, atomizing, dusting, scattering, coating, dressing, and pouring are chosen in accordance with the intended objectives of the application and the prevailing circumstances. One method of applying the active ingredient or agrochemical composition containing at least one of the stated compounds is application to the plants (i.e. foliar application). However, the active ingredient can also penetrate the plant through the roots via the soil (i.e. soil application). This may be in the form of either a liquid application to the soil (drench) or a granular application.

The active ingredient can also be applied to plant propagation material such as seeds (fruits, tubers or grains) or plant cuttings, in either liquid form (coating) or in solid form (dressing). Seeds, for example, can be dressed before sowing. The compounds of the invention can also be applied to grains either by impregnating the grains with a liquid formulation of by coating them with a solid formulation. The composition can also be applied to the locus of planting when planting the propagation material, for example to the seed furrow during sowing.

Advantageous rates of application are normally from 10 g to 50kg of active ingredient (a.i.) per hectare, preferably 100 g to 2 kg a.i./ha, most preferably 100 g to 600 g a.i./ha. The active ingredients of the stated compounds are typically used in the form of compositions and can be applied to the plant, or to parts of the plant either simultaneously or in succession with further active ingredients. These further active ingredients can be fertilizers, additional micronutrients, or other plant growth affecting compounds. They can, however, also be selective herbicides, insecticides, bactericides, nematocides, insecticides, and molluscicides, as well as other fungicides.

Preparation of Starting Material
Fermentation Production of Sordarin

The following media are used in the fermentation of *Rosellinia subiculata* (ATCC 74386) and ATCC 74387 in the production of sordarin.

| SEED MEDIUM 1 | |
| --- | --- |
| Component | g/L |
| Yeast extract | 4.0 |
| Malt extract | 8.0 |
| Glucose | 4.0 |
| Junlon | 1.5 |

The medium was prepared with distilled water, the pH adjusted to 7.0 prior to sterilization, and was dispensed at 50 ml/250 ml unbaffled Erlenmeyer flask. Cotton closures were used. Sterilization was at 121° C. for 20 minutes.

| SEED MEDIUM 2 | | | |
| --- | --- | --- | --- |
| | | Trace elements solution | |
| Component | (g/l) | Component | (g/l) |
| Corn steep liquor (dried) | 2.5 | $FeSO_4.7H_2O$ | 1.0 |
| Tomato paste | 40.0 | $MnSO_4.4H_2O$ | 1.0 |
| Oat flour | 10.0 | $CuCl_2.2H_2O$ | 0.025 |
| Glucose | 10.0 | $CaCl_2.H_2O$ | 0.1 |
| Trace elements solution | 10.0 ml/L | $H_3BO_3$ | 0.056 |
| | | $(NH_4)_6MoO_{24}.4H_2O$ | 0.019 |
| | | $ZnSO_4.7H_2O$ | 0.2 |
| | | Trace elements prepared in 0.6N HCl | |

The medium was prepared with distilled water, the pH adjusted to 6.8 prior to sterilization, and was dispensed at 50 ml/250 ml unbaffled Erlenmeyer flask. Cotton closures were used. Sterilization was at 121° C. for 20 minutes.

Solid Production Medium 1

1. Solid portion:

Add 675 cc vermiculite to a 2-liter roller bottle. Plug with latex closure; autoclave for 60 min., plus 30 min. dry.

2. Liquid portion:

To a 500 ml bottle, add 220 ml of the following:

| Component | g/L |
|---|---|
| Glucose | 150.0 |
| Glycerol | 20.0 |
| Yeast extract | 4.0 |
| NaNO$_3$ | 1.0 |
| Monosodium Glutamate | 3.0 |
| Na$_2$HPO$_4$ | 0.5 |
| MgSO$_4$.7H$_2$O | 1.0 |
| K-elements | 1.0 ml/L |
| CaCO$_3$ | 8.0 |

| K-elements Component | (g/l) |
|---|---|
| FeCl$_3$.6H$_2$O | 5.8 |
| MnSO$_4$.H$_2$O | 0.1 |
| CoCl$_2$.6H$_2$O | 0.02 |
| CuSO$_4$.5H$_2$O | 0.015 |
| Na$_2$MoO$_4$.2H$_2$O | 0.012 |
| ZnCl$_2$ | 0.02 |
| SnCl$_2$.2H$_2$O | 0.005 |
| H$_3$BO$_3$ | 0.01 |
| KCl | 0.02 |
| HCl (concentrated) | 2.0 ml/L |

The medium was prepared with distilled water, pH to 7.0 prior to sterilization. Glucose was autoclaved separately. It was dispensed in 500 ml bottles and autoclaved at 121° C. for 15 minutes.

Liquid Production Medium 1

| Component | g/L |
|---|---|
| Glycerol | 75.0 |
| Glucose | 75.0 |
| Tomato paste | 5.0 |
| NZ amine Type A | 4.0 |
| Ardamine PH | 5.0 |
| K$_2$HPO$_4$ | 0.5 |
| MgSO$_4$.7H$_2$O | 0.25 |
| KCl | 0.25 |
| ZnSO$_4$.7H$_2$O | 0.5 |
| CaCO$_3$ | 10.0 |

The medium was prepared with distilled water, pH to 7.0 prior to sterilization. The medium was dispensed at 50 ml per 250 ml unbaffled Erlenmeyer flask. The flasks were closed with cotton and autoclaved at 121° C. for 20 minutes.

Solid Production Medium 2

1. Solid portion:

Add 675 cc vermiculite to a 2-liter roller bottle. Plug with latex closure; autoclave for 60 min., plus 30 m in. dry.

2. Liquid portion:

To a 500 ml bottle, add 220 ml of the following:

| Component | g/L |
|---|---|
| Sucrose | 60.0 |
| Glucose | 80.0 |
| Glycerol | 60.0 |
| Citric Acid | 15.0 |
| NZ amine Type A | 5.0 |
| NaNO$_3$ | 1.0 |
| KH$_2$PO$_4$ | 0.5 |
| MgSO$_4$.7H$_2$O | 0.5 |
| CaCO$_3$ | 0.5 |

| | |
|---|---|
| K-elements | 1 ml/L |

| K-elements Component | (g/l) |
|---|---|
| FeCl$_3$.6H$_2$O | 5.8 |
| MnSO$_4$.H$_2$O | 0.1 |
| CoCl$_2$.6H$_2$O | 0.02 |
| CuSO$_4$.5H$_2$O | 0.015 |
| Na$_2$MoO$_4$.2H$_2$O | 0.012 |
| ZnCl$_2$ | 0.02 |
| SnCl$_2$.2H$_2$O | 0.005 |
| H$_3$BO$_3$ | 0.01 |
| KCl | 0.02 |
| HCl (concentrated) | 2.0 ml/L |

The medium was prepared with distilled water, pH to 7.0 prior to sterilization. It was dispensed at 220 ml per 500 ml bottle and autoclaved at 121° C. for 15 minutes.

Liquid Production Medium 2

The composition is the same as the liquid portion of Solid Production Medium 1. The medium was prepared with distilled water, pH to 7.0 prior to sterilization. Glucose was autoclaved separately. The medium was dispensed at 50 ml per 250 ml unbaffled Erlenmeyer flask. The flasks were closed with cotton and autoclaved at 121° C. for 15 minutes.

Production of Sordarin by Fermentation of *Rosellina subiculata* (MF6239, ATCC 74386)

1. CULTURE: A portion of the agar slant containing the culture was aseptically transferred to seed medium 1 (50 ml/250 ml unbaffled flask). This was incubated on a 2-inch throw gyratory shaker, 220 rpm for 5 days at 25° C., 85% relative humidity (rh), to obtain biomass. Portions of the biomass were transferred into sterile vials containing glycerol and frozen (as frozen vegetative mycelia (FVM)). These were maintained in a final concentration of 10–15% glycerol at −75° C. Secondary FVMs were prepared from a primary FVM by transferring 1.0 ml of the thawed primary FVM into seed medium 2, incubating 7 days at 25° C., 220 rpm and freezing as above.

2. SEED: A frozen vial (FVM) of MF6239 was thawed to room temperature and used to inoculate seed cultures with 1.0 ml per 50 ml seed medium 2. These were grown on a gyratory shaker (220 rpm) for 7 days at 25° C., 85% rh.

3. PRODUCTION: On solid production medium. An aliquot (10–12 ml) of the seed was placed into 220 ml of the liquid portion of solid production medium 1. This flask was swirled vigorously to disperse the biomass. The contents were dispensed by pouring into a 2L roller culture vessel which contained 675 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 70% rh for 17 days, to obtain a secondary metabolite in the fermentation medium.

In liquid production medium. Seed cultures were inoculated as described above. An aliquot of the seed (1.5 ml) was used to inoculate each production flask, containing 50 ml/250 ml flask of liquid production medium 1. Flasks were incubated on a gyratory shaker (220 rpm) for 7–21 days at 25° C., 50–85% rh.

Production of Sordarin by Fermentation of MF6232 (ATCC 74387)

1. CULTURE: A portion of the agar slant containing MF6232 was aseptically transferred to seed medium 1 (50 ml/250 ml unbaffled flask). This was incubated on a 2-inch throw gyratory shaker, 220 rpm for 3 days at 25° C., 85% relative humidity (rh), to obtain biomass. Portions of the biomass were transferred into sterile vials containing glycerol and frozen (as FVM). These were maintained in a final concentration of 10–15% glycerol at −75° C. Secondary FVMs were prepared from a primary FVM by transferring 1.0 ml of the thawed primary FVM into seed medium 2 (composition below), incubating 7 days, 25° C., 220 rpm, and freezing as above.

2. SEED: A frozen vial (FVM) of MF6232 was thawed to room temperature and used to inoculate seed cultures with 1.0 ml per 50 ml seed medium 2. These were grown on a gyratory shaker (220 rpm) for 7 days at 250C, 85% rh.

3. PRODUCTION: On solid production medium. An aliquot (10–12 ml) of the seed was placed into 220 ml of solid production medium 2. This was swirled vigorously to disperse the biomass. The contents were dispensed by pouring into a 2L roller culture vessel which contained 675 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 70% rh for 21 days, to obtain a secondary metabolite in the fermentation medium.

In liquid production medium. Seed cultures were inoculated as described above. An aliquot of the seed (1.5 ml) was used to inoculate each production flask, containing 50 ml/250 ml flask of liquid production medium 2. Flasks were incubated on a gyratory shaker (220 rpm) for 7–21 days at 25° C., 50–85% rh.

Large Scale Production of Sordarin by MF6232 (ATCC 74387)

The liquid portion of solid production medium 1 was used for both the seed and production fermenters. Cerelose, added post-sterilely, in the seed fermenter medium was 30 g/L while that of the production fermenter medium was 150 g/L. Seed fermenters were inoculated with 2 L of culture grown in shaker flasks. These fermenters were permitted to grow at 25° C. for 30 hours until the oxygen uptake rate was about 3 mmol/L-hr. At 30 hours, 25 L of fermenter seed culture was transferred to the production fermenter.

Growth in the production fermenter reached 8–10 mmol/L-hr after 50 hours and declined to between 5–7 by the end of the cultivation. Dissolved oxygen was controlled by increasing agitation. Broth pH was not controlled and generally decreased to 5.3 at 200 hours. The temperature was 25° C.

After 280 hours of growth the fermentation was terminated and the preparations for harvest begun. The pH was adjusted to about 12 with sodium hydroxide and the batch aged for 20 hours at fermentation temperature. The pH was then adjusted to 6.0 with sulfuric acid prior to transfer into drums for further processing.

Isolation of Sordarin

Isolation I

A methyl ethyl ketone extract of the fermentation of culture MF6232 (ATCC 74387) corresponding to 64 mL of whole broth was concentrated to dryness in vacuo (365 mg). This material was dissolved in 2 parts methanol in 98 parts methylene chloride to a final volume of 4.6 ml. A 4.3 ml portion (341 mg) was applied to a 60 ml silica gel 60 (0.040–0.0630 mm, 230–400 mesh, E. Merck) flash chromatography column equilibrated with 2 percent methanol in methylene chloride. The column was eluted by a step gradient of 240 ml each of 2, 5, 10, and 30 percent methanol in methylene chloride followed by 120 ml of methanol. Sixteen 15 ml fractions were collected from each solvent system. The product rich fractions 39–56 were determined by biological assay.

The crude fraction pool was concentrated to dryness in vacuo (103.1 mg). A 34.4 mg portion of this sample was further purified by HPLC separation (Zorbax Rx-C8, 5 μm, 9.4 mm×250 mm, eluted with mobile phase consisting of 20% acetonitrile/80% aqueous 0.01M $K_2HPO_4$ adjusted to pH 6.9 with concentrated $H_3PO_4$, flow rate 4 ml/min. at 40° C., diode array detection). Four milliliter fractions were collected. The product rich fractions 16–20 were pooled and concentrated in vacuo to approximately twenty-five percent of the original volume. The concentrate was doubly extracted with an equal volume of ethyl acetate and the ethyl acetate layers were washed with an equal volume of brine, dried over anhydrous $Na_2SO_4$ and concentrated in vacuo to yield 3.7 mg of sordarin.

Isolation II

A methyl ethyl ketone extract of the batch -004Y fermentation of culture MF6232 (ATCC74387) corresponding to 980 mL of whole broth was concentrated to dryness in vacuo (4.9 g). This material was dissolved in 1 part methanol in 9 parts methylene chloride to a final volume of 21.5 ml. A 21 ml portion (4.8 g) was applied to a 500 milliliter silica gel 60 (0.040–0.0630 mm, 230–400 mesh, E. Merck) chromatography column equilibrated with 2 percent methanol in methylene chloride. The column was eluted at a flowrate of 25 ml/min. by a step gradient beginning with 1 liter each of 2 and 5 percent methanol in methylene chloride followed by 2 liters of 15 percent methanol. The column elution was completed with 1 liter each of 30 and 100 percent methanol. Twenty-five milliliter fractions were collected. Product rich fractions 75–85 and 111–121 were determined by biological assay and contained Compound I by RP HPLC analysis under acidic conditions.

The crude fraction pools, 75–85 and 111–121 were concentrated, separately, to dryness in vacuo (69.3 mg and 95.3 mg, respectively). Two 34 mg portions of pool 75–85 were further purified by two identical HPLC separations (Zorbax Rx-C8, 7 μm, 21.2 mm×250 mm, eluted with mobile phase consisting of 40% acetonitrile/60% $H_2O$ with 0.1% $H_3PO_4$ overall, flow rate 20 ml/min. at 25° C., 220 nm). Ten milliliter fractions were collected. The product rich fractions 27–31 from both runs were pooled together and concentrated in vacuo to approximately forty percent of the original volume. The concentrate was extracted with an equal volume of ethyl acetate and washed with an equal volume of brine, dried over anhydrous $Na_2SO_4$ and concentrated in vacuo to yield 27 mg of sordarin. Two 46 mg portions of pool 111–121 were also further purified under the identical HPLC conditions listed above. Fractions 25–28 from both runs were combined and prepared as described above to yield an additional 17 mg of sordarin.

Preparation of Sordaricin Benzyl Ester

Sordarin (2 mg) was dissolved in 1 mL of acetone. Concentrated HCl (0.2 mL) was added. The mixture was stirred at room temperature for 1 day. After dilution with water and aqueous work-up ($CH_2Cl_2$), the organic fraction was dried over $Na_2SO_4$, filtered and concentrated in vacuo The mixture was dissolved in 2 mL of DMF to which was added 0.1 mL of benzyl bromide, followed by excess solid $NaHCO_3$. The mixture was stirred at room temperature overnight, and was then concentrated in vacuo. Chloroform was added to the mixture which was filtered to remove the $NaHCO_3$. The filtrate was concentrated in vacuo and purified by preparative thin layer chromatography (PTLC) to yield 1.0 mg of sordaricin benzyl ester. $^1$H NMR (CDCl$_3$): δ 0.51 (3H, d, J=6.9), 0.82 (3H, d, J=6.6), 0.91 (1H, m), 1.0 (3H, d, J=6.6), 1.18 (1H, d, J=12.6), 1.50–2.00 (9H, m), 2.24 (1H, m), 2.51 (1H, m), 3.48 (1H, d, J=11.0), 3.87 (1H, d, J=11.0), 5.11 (1H, d, J=11.7), 5.31 (1H, d, J=11.7), 6.04 (1H, d, J=2.1), 7.31–7.40 (5H, m), 9.62 (1H, s).

Preparation of Sordaricin p-methoxybenzyl Ester

The same procedure for the preparation of sordaricin benzyl ester was followed, with the use of 4-methoxybenzyl chloride instead of benzyl bromide. $^1$H NMR (CDCl$_3$): δ 0.51 (3H, d, J=6.9), 0.82 (3H, d, J=6.9), 1.00 (3H, d, J=6.9), 0.90–2.00 (11H, m), 2.23 (1H, m), 2.49 (1H, t, J=3.8), 3.79 (3H, s), 4.61 (2H, s), 5.05 (1H, d, J=11.7), 5.26 (1H, d, J=11.7), 6.03 (1H, d, J=3.2), 6.88 (2H, d, J=8.7), 7.28 (2H, d, J=8.7), 9.60 (1H, s).

Preparation of Sordaricin Allyl Ester

A similar procedure for the preparation of sordaricin benzyl ester is followed, with the use of allyl bromide instead of benzyl bromide. In this manner, the title compound may be obtained.

Preparation of Sordaricin

To a MeOH solution of sordaricin benzyl ester (0.6 mg) was added Pearlman's catalyst. The mixture was stirred under hydrogen (balloon pressure) for 15 minutes. After filtration through cotton wool and concentration in vacuo, 0.4 mg of sodaricin was obtained. $^1$H NMR (CDCl$_3$): δ 0.82 (3H, d, J=6.8), 0.98 (3H, d, J=6.6), 1.01 (3H, d, J=6.9), 1,23 (1H, m), 1.25 (1H, d, J=12.6), 1.58–2.10 (9H, m), 2.34 (1H, m), 2.41 (1H, t, J=3.6), 3.45 (1H, d,=11.0), 4.14 (1H, d, J=11.0), 6.05 (1H, d, J=3.0), 9.75 (1H, s).

The following examples are provided to more fully illustrate the invention, and are not to be construed as limiting the scope of the invention in any manner.

EXAMPLE 1

[1R-(1,3aβ,4β,4aβ,7β,7aα;8aβ)]8a-[(acetyloxy)methyl]-4-formyl-4,4a,5,6,7,7a,8,8a-octahydro-7-methyl-3-(1-methylethyl)-1,4-methano-s-indacene-3a(1H)-carboxylic Acid Sordaricin benzyl ester (1.0 mg) was dissolved in 1 mL of pyridine and 1 mL of acetic anhydride. A catalytic amount of 4-(N,N-dimethylaminopyridine) (DMAP) was added, and the mixture was stirred at room temperature for 30 minutes. After concentration in vacuo and purification by PTLC, 1.0 mg of the benzyl ester of the title compound was obtained. This compound was dissolved in 1 mL of MeOH to which Pearlman's catalyst was added. The mixture was stirred under hydrogen (balloon pressure) for 15 minutes. After filtration through cotton wool and concentration in vacuo, the title compound was obtained. $^1$H NMR (CDCl$_3$): δ 0.77 (3H, d, J=6.6), 0.97 (3H, d, J=6.6), 1.01 (3H, d, J=6.8), 1.22 (1H, m), 1.32 (1H, d, J=12.5), 1.72–2.10 (9H, m), 2.02 (3H, s), 2.33 (1H, m), 2.70 (1H, t, J=3.9), 4.22 (1H, d, J=10.7), 4.28 (1H, d, J=10.7), 6.07 (1H, d, J=2.3), 9.68 (1H, s).

EXAMPLE 2

[1R-(1α,3β,4β,4aβ,7β,7aα,8aβ)]8a-[(undecanoyloxy)methyl]-4-formyl-4,4a,5,6,7,7a,8,8a-octahydro-7-methyl-3-(1-methylethyl)-1,4-methano-s-indacene-3a(1H)-carboxylic Acid To a tetrahydrofuran (THF) solution of undecanoic acid (30 mg) was added NEt$_3$ (34 μL), followed by 2,4,6-trichlorobenzoyl chloride (25 μL). The mixture was stirred at room temperature for 15 minutes. Sordaricin benzyl ester (1.0 mg) in 1 mL of THF was then added to this mixture, followed by the addition of DMAP (20 mg). This mixture was stirred at room temperature for 1 hour. After purification by PTLC, the benzyl ester of the title compound was obtained. This undecanoate was dissolved in 1 mL of MeOH to which Pearlman's catalyst was added. The mixture was stirred under hydrogen (balloon pressure) for 15 minutes. After filtration through cotton wool and concentration in vacuo, the title compound was obtained. $^1$H NMR (CDCl$_3$): δ 0.77 (3H, d, J=6.6), 0.86 (3H, t, J=6.8), 0.97 (3h, d, J=6.6), 1.10 (3H, d, J=6.8), 0.96–1.02 (2H, m), 1.2–1.3 (16H, m), 1.56–2.10 (9H, m), 2.26 (2H, t, J=7.6), 2.34 (1H, m), 2.68 (1H, t, J=3.9), 4.20 (1H, d, J=10.8), 4.31 (1H, d, J=10.8), 6.06 (1H, d, J=2.3), 9.68 (1H, s).

EXAMPLE 3

[1R-(1α,3aβ,4β,4aβ,7β,7aα,8aβ)]8a-[(propanoyloxy)methyl]-4-formyl-4,4a,5,6,7,7a,8,8a-octahydro-7-methyl-3-(1-methylethyl)-1,4-methano-s-indacene-3a(1H)-carboxylic Acid To a CH$_2$Cl$_2$ solution of sordaricin benzyl ester (0.5 mg) was added NEt$_3$ (0.2 mL), followed by propionyl chloride (0.1 mL). A catalytic amount of DMAP was added. The mixture was stirred at room temperature overnight. After purification by PTLC, the benzyl ester of the title compound was obtained. This compound was dissolved in 1 mL of MeOH and Pearlman's catalyst was added. The mixture was stirred under hydrogen (balloon pressure) for 15 minutes. After filtration through cotton wool and concentration in vacuo, the title compound was obtained. $^1$H NMR (CDCl$_3$): δ 0.78 (3H, d, J=6.6), 0.97 (3H, d, J=6.8), 1.01 (3H, d, J=6.9), 1.12 (3H, t, J=7.6), 1.21 (1H, m), 1.32 (1H, d, J=12.5), 1.70–2.10 (9H, m), 2.29 (2H, t, J=7.6), 2.32 (1H, m), 2.69 (1H, t, J=3.7), 4.21 (1H, d, J=11.0), 4.32 (1H, d, J=11.0), 6.07 (1H, d, J=3.4), 9.70 (1H, s).

EXAMPLE 4

[1R-(1α,3aβ,4β,4aβ,7β,7aα,8aβ)]8a-[(methoxycarbonyloxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 3 was followed, with the use of methyl chloroformate instead of propionyl chloride. $^1$H NMR (CDCl$_3$): δ 0.98 (3H, d, J=6.9), 1.01 (3H, d, J=6.9), 1.18 (3H, d, J=6.9), 1.22 (1H, m), 1.32 (1H, d, J=12.5), 1.60–2.10 (9H, m), 2.33 (1H, m), 2.75 (1H, t, J=3.7), 3.75 (3H, s), 4.32 (1H, d, J=10.3), 4.39 (1H, d, J=10.3), 6.10 (1H, d, J=2.5), 9.65 (1H, s).

EXAMPLE 5

[1R-(1α,3aβ,4β,4aβ,7β,7aα,8aβ)]8a-[(propylaminocarbonyloxy)methyl]-4-formyl-4,4a,5,6,7,7a,8,8a-octahydro-7-methyl-3-(1-methylethyl)-1,4-methano-s-indacene-3a(1H)-carboxylic Acid To a CHCl$_3$ solution of sordaricin benzyl ester (0.5 mg) was added n-propyl isocyanate (0.1 mL) and a catalytic amount of DMAP. The mixture was refluxed for 4 hours. After concentration in vacuo and purification by PTLC, the benzyl ester of the title compound was obtained. This derivative was dissolved in 1 mL of MeOH and Pearlman's catalyst was added. The mixture was stirred under hydrogen (balloon pressure) for 15 minutes. After concentration in vacuo and purification by PTLC, the title compound was obtained. $^1$H NMR (CDCl$_3$): δ 0.78 (3H, d, J=6.4), 0.90 (3H, t, J=7.4), 0.96 (3H, d, J=7.1), 1.00 (3H, d, J=6.7), 1.22 (1H, m), 1.31 (1H, d, J=12.5), 1.50 (2H, m), 1.50–2.10 (9H, m), 2.32 (1H, m), 2.66 (1H, m), 3.10 (2H, m), 4.22 (1H, d, J=10.5), 4.30 (1H, d, J=10.5), 4.60 (1H, br), 6.07 (1H, s), 9.70 (1H, s).

EXAMPLE 6

[1R-(1α,3aβ,4β,4aβ,7β,7aα,8aβ)]8a-[(methoxymethoxy)methyl]4-formyl-4,4a,5,6,7,7a,8,8a-octahydro-7-methyl-3-(1-methylethyl)-1,4-methano-s-indacene-3a(1H)-carboxylic Acid To a $CH_2Cl_2$ solution of sordaricin benzyl ester (0.5 mg) was added diisopropylethylamine (0.2 mL), followed by methoxymethyl chloride (MOMCl) (0.1 mL) at 0° C. The mixture was stirred at room temperature overnight. After concentration in vacuo and purification by PTLC, the benzyl ester of the title compound was obtained. This derivative was dissolved in methanol and Pearlman's catalyst (palladium hydroxide on carbon) was added. The mixture was stirred under hydrogen (balloon pressure) until removal of the benzyl group was complete as determined by TLC. After concentration in vacuo and purification by PTLC, the title compound was obtained. $^1$H NMR ($CDCl_3$): δ 0.82 (3H, d, J=6.9), 0.96 (3H, d, J=6.7), 1.02 (3H, d, J=6.9), 1.23 (1H, m), 1.28 (1H, d, J=12.5), 1.50–2.10 (9H, m), 2.32 (1H, m), 2.48 (1H, m), 3.35 (3H, s), 3.44 (1H, d, J=9.8), 4.00 (1H, d, J=9.8), 4.61 (2H, AB q, J=6.7), 6.05 (1H, d, J 2.6), 9.83 (1H, s).

EXAMPLE 7

[1R-(1α,3aβ,4β,4aβ,7β,7aα,8aβ)]8a-[((methoxyethoxy)methoxy)-methyl]-4-formyl-4,4a,5,6,7,7a,8,8a-octahydro-7-methyl-3-(1-methylethyl)-1,4-methano-s-indacene-3a(1H)-carboxylic Acid The procedure of Example 6 was followed, with the use of methoxyethoxymethyl chloride instead of MOMCl. $^1$H NMR ($CDCl_3$): δ 0.81 (3H, d, J=6.4), 0.96 (3H, d, J=7.4), 1.02 (3H, d, J=6.9), 1.10 (1H, m), 1.15 (1H, d, J=6.4), 1.50–2.10 (9H, m), 2.33 (1H, m), 2.45 (1H, t, J=3.7), 3.2–3.6 (6H, m), 3.53 (3H, s), 3.93 (1H, d, J=9.3), 3.99 (1H, d, J=9.3), 6.04 (1H, d, J=2.1), 9.90 (1H, s).

EXAMPLE 8

[1R-(1α,3aβ,4β,4aβ,7β,7aα,8aβ)]8a-[(octyloxymethoxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 6 was followed, with the use of chloromethyl octyl ether instead of MOMCl. $^1$H NMR ($CDCl_3$): δ 0.82 (3H, d, J=6.9), 0.86 (3H, t, J=7.1), 0.96 (3H, d, J=6.7), 1.02 (3H, d, J=6.9), 1.20–1.30 (14H, m), 1.5–2.1 (9H, m), 2.32 (1H, m), 2.47 (1H, t, J=3.7), 3.44 (1H, d, J=9.4), 3.49 (2H, t, J=6.6), 3.99 (1H, d, J=9.4), 4.67 (2H, s), 6.05 (1H, d, J=2.3), 9.84 (1H, s).

EXAMPLE 9

[1R-(1α,3aβ,4β,4aβ,7β,7aα,8aβ)]8a-[(methoxy)methyl]-4-formyl-4,4a,5,6,7,7a,8,8a-octahydro-7-methyl-3-(1-methylethyl)-1,4-methano-s-indacene-3a(1H)-carboxylic Acid To a dimethylformamide (DMF) solution of sordaricin benzyl ester was added excess methyl iodide (0.1 mL), followed by NaH (20 mg of a 60% oil dispersion). The mixture was stirred at room temperature overnight. After concentration in vacuo and purification by PTLC, the benzyl ester of the title compound was obtained. This derivative was dissolved in methanol and palladium hydroxide on carbon (Pearlman's catalyst) was added. The mixture was stirred under hydrogen (balloon pressure) until removal of the benzyl group was complete as determined by TLC. After concentration in vacuo and purification by PTLC, the title compound was obtained. $^1$H NMR ($CDCl_3$): δ 0.82 (3H, d, J=6.9), 0.96 (3H, d, J=6.6), 1.03 (3H, d, J=6.9), 1.20–2.20 (11H, n), 2.33 (1H, m), 2.36 (1H, t, J=3.7), 3.26 (1H, d, J=9.1), 3.38 (3H, s), 3.93 (1H, d, J=9.1), 6.03 (1H, d, J=2.8), 9.88 (1H, s).

EXAMPLE 10

[1R-(1α,3aβ,4β,4aβ,7β,7aα,8aβ)]8a-[(ethoxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of ethyl iodide instead of methyl iodide. 1H NMR ($CDCl_3$): δ 0.83 (3H, d, J=6.8), 0.95 (3H, d, J=6.6), 1.02 (3H, d, J=6.9), 1.22 (3H, t, J=7.0), 1.24 (2H, m), 1.78–2.16 (9H, m), 2.30–2.38 (2H, m), 3.25 (1H, d, J=8.4), 3.54 (2H, m), 3.98 (1H, d, J=8.4), 6.02 (1H, m), 9.89 (1H, s).

EXAMPLE 11

[1R-(1α,3aβ,4β,4aβ,7β,7aα,8aβ)]8a-[(propyloxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of allyl bromide instead of methyl iodide. $^1$H NMR ($CDCl_3$): δ 0.83 (3H, d, J=6.9), 0.91 (3H, t, J=7.5), 0.95 (3H, d, J=6.9), 1.02 (3H, d, J=6.8), 1.24 (1H, m), 1.26 (1H, d, J=12.5), 1.50–2.15 (11H, m), 2.33 (1H, m), 2.34 (1H, m), 3.23 (1H, d, J=9.2), 3.44 (2H, m), 3.99 (1H, d, J=9.2), 6.02 (1H, d, J=2.1), 9.90 (1H, s).

EXAMPLE 12

[1R-(1α,3aβ,4β,4aβ,7β,7aα,8aβ)]8a-[(2-methylpropyloxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of 2-bromomethyl-1-propene instead of methyl iodide. $^1$H NMR ($CDCl_3$): δ 0.83 (3H, d, J=7.1), 0.89 (3H, d, J=6.7), 0.90 (3H, d, J=6.9), 0.95 (3H, d, J=6.8), 1.23 (1H, m), 1.26 (1H, d, J=12.8), 1.50–2.16 (10H, m), 2.32 (1H, m), 2.34 (1H, t, J=3.7), 3.18 (1H, dd, J=6.9, 9.4), 3.21 (1H, d, J=9.4), 3.31 (1H, dd, J=6.4, 9.4), 4.00 (1H, d, J=9.4), 6.02 (1H, dd, J=1.2, 3.2), 9.90 (1H, s).

EXAMPLE 13

[1R-(1α,3aβ,4β,4aβ,7β,7aα,8aβ)]8a-[(butyloxy)methyl]4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of 1-iodobutane or crotyl chloride instead of methyl iodide. $^1$H NMR ($CDCl_3$): δ 0.82 (3H, d, J=7.1), 0.90 (3H, t, J=7.5), 0.95 (3H, d, J=6.7), 1.02 (3H, d, J=6.9), 1.20–1.28 (2H, m), 1.34 (2H, m), 1.50–2.16 (11H, m), 2.32 (1H, m), 2.35 (1H, t, J=3.7), 3.23 (1H, d, J=9.1), 3.46 (2H, m), 3.98 (1H, d, J=9.1), 6.02 (1H, d, J 2.3), 9.89 (1H, s).

EXAMPLE 14

[1R-(1α,3aβ,4β,4aβ,7β,7aα,8aβ)]8a-[(pentyloxy) methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of trans-1-bromo-2-pentene or 1-iodopentane instead of methyl iodide. $^1$H NMR (CDCl$_3$): δ 0.83 (3H, d, J=6.9), 0.87 (3H, t, J=7.1), 0.96 (3H, d, J=6.8), 1.02 (3H, d, J=6.9), 1.20–1.34 (6H, m), 1.50–2.16 (11H, m), 2.32 (1H, m), 2.34 (1H, t, J=3.7), 3.22 (1H, d, J=9.2), 3.46 (2H, m), 3.98 (1H, d, J=9.2), 6.02 (1H, d, J=2.1), 9.90 (1H, s).

EXAMPLE 15

[1R-(1α,3aβ,4β,4aβ,7β,7aα,8aβ)]8a-[(hexyloxy) methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of 1-iodohexane instead of methyl iodide. $^1$H NMR (CDCl$_3$): δ 0.83 (3H, d, J=7.1), 0.86 (3H, t, J=7.3), 0.95 (3H, d, J=6.6), 1.02 (3H, d, J=6.6), 1.20–1.32 (8H, m), 1.50–2.16 (1H, m), 2.32 (1H, m), 2.34 (1H, t, J=3.7), 3.22 (1H, d, J=9.1), 3.46 (2H, m), 3.98 (2H, d, J=9.1), 6.02 (1H, d, J=2.1), 9.90 (1H, s).

EXAMPLE 16

[1R-(1α,3aβ,4β,4aβ,7β,7aα,8aβ)]8a-[(S-2-hydroxypropyloxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of the benzenesulfonate of (R)-glycidol instead of methyl iodide. $^1$H NMR (CDCl$_3$): δ 0.82 (3H, d, J=6.8), 0.96 (3H, d, J=6.6), 1.02 (3H, d, J=6.9), 1.15 (3H, d, J=6.4), 1.24 (1H, m), 1.27 (1H, d, J=12.6), 1.60–2.10 (9H, m), 2.33 (1H, m), 2.46 (1H, t, J=3.9), 3.34 (1H, dd, J=7.4, 10.0), 3.40 (1H, dd, J=3.4, 10.0), 3.43 (1H, d, J=9.4), 3.92 (1H, d, J=9.4), 3.99 (1H, m), 6.04 (1H, d, J=2.3), 9.83 (1H, s).

EXAMPLE 17

[1R-(1α,3aβ,4β,4aβ,7β,7aα,8aβ)]8a-[(R-2-hydroxypropyloxy)methyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of the benzenesulfonate of (S)-glycidol instead of methyl iodide. 1H NMR (CDCl$_3$): δ 0.82 (3H, d, J=6.8), 0.96 (3H, d, J=6.6), 1.02 (3H, d, J=6.9), 1.15 (3H, d, J=6.9), 1.23 (1H, m), 1.26 (1H, t, J=12.6), 1.50–2.10 (9H, m), 2.33 (1H, m), 2.45 (1H, t, J=3.9), 3.30 (1H, dd, J=7.5, 10.0), 3.40 (1H, dd, J=3.4, 10.0), 3.52 (1H, d, J=9.4), 3.97 (1H, d, J=9.4), 3.99 (1H, m), 6.04 (1H, d, J=2.6), 9.83 (1H, s).

EXAMPLE 18

[1R-(1α,3aβ,4β,4aβ,7β,7aα,8aβ)]8a-[n-heptyloxymethyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of hepyt-2-yn-1-ol benzenesulfonate instead of MeI. MS (CI): m/z=448 (M+NH$_4$).

EXAMPLE 19

[1R-(1α,3aβ,4β,4aβ,7β,7aα,8aβ)]8a-[n-octyloxymethyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of oct-2-yn-1-ol benzenesulfonate instead of MeI. MS (CI): m/z=462 M+NH$_4$).

EXAMPLE 20

[1R-(1α,3aβ,4β,4aβ,7β,7aα,8aβ)]8a-[n-nonyloxymethyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of non-2-yn-1-ol benzenesulfonate instead of MeI. MS (CI): m/z=476 (M+NH$_4$).

EXAMPLE 21

[1R-(1α,3aβ,4β,4aβ,7β,7aα,8aβ)]8a-[n-decyloxymethyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of dec-2-yn-1-ol benzenesulfonate instead of MeI. MS (CI): m/z=490 (M+NH$_4$).

EXAMPLE 22

[1R-(1α,3aβ,4β,4aβ,7β,7aα,8aβ)]8a-[3-methylbut-1-oxymethyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of 1-iodo-3-methylbutane instead of MeI. MS (CI): m/z=403 (M+H).

EXAMPLE 23

[1R-(1α,3aβ,4β,4aβ,7β,7aα,8aβ)]8a-[2-propoxymethyl]-4-formyl-4,4a,5,6,7,7a,8,8a-octahydro-7-methyl-3-(1-methylethyl)-1,4-methano-s-indacene-3a(1H)-carboxylic Acid The procedure of Example 9 was followed, with the use of 2-iodopropane instead of MeI. MS (CI): m/z=375 (M+H).

EXAMPLE 24

[1R-(1α,3aβ,4β,4aβ,7β,7aα,8aβ)]8a-[2-(tetrahydropyranyloxy)methyl]-4-formyl-4,4a,5,6,7,7a,8,8a-octahydro-7-methyl-3-(1-methylethyl)-1,4-methano-s-indacene-3a(1H)-carboxylic Acid To a solution of sordaricin benzyl ester (10 mg) in 3 mL of CH$_2$Cl$_2$ was added 3,4-dihydro-2H-pyran (50 μL) and a catalytic amount of PPTS. The mixture was stirred at room temperature overnight. NEt$_3$ (1 mL) was added and the mixture was concentrated in vacuo. After purification by PTLC, the benzyl ester of the title compound was obtained. To a MeOH solution of this benzyl ester was added Pearlman's catalyst. The mixture was stirred under hydrogen (balloon pressure) for 15 minutes. The mixture was filtered through cotton. The filtrate was concentrated in vacuo to give the title compound. MS (CI): m/z=434 (M+NH$_4$).

EXAMPLE 25

[1R-(1α,3aβ,4β,4aβ,7β,7aα,8aβ)]8a-[(1-ethoxyethoxy)methyl)]-4-formyl-4,4a,5,6,7,7a,8,8a-octahydro-7-methyl-3-(1-methylethyl)-1,4-methano-s-indacene-3a(1H)-carboxylic Acid The same procedure for the preparation of the compound from Example 24 was followed with the use of ethyl vinyl ether instead 3,4-dihydro-2H-pyran. $^1$H NMR (CDCl$_3$): δ 0.78–2.50 (28H, m), 3.20–4.20 (4H, m), 4.60–4.80 (1H, m), 6.03–6.10 (1H), 9.84–9.86 (1H).

EXAMPLE 26

[1R-(1α,3aβ,4β,4aβ,7β,7aα,8aβ)]8a-[(benzyloxy)methyl)]-4-formyl-4,4a,5,$^6$,$^7$,7a,8,8a-octahydro-7-methyl-3 -(1-methylethyl)-1,4-methano-s-indacene-3a(1H)-carboxylic Acid To a DMF solution of sordaricin p-methoxybenzyl ester was added excess benzyl bromide and sodium hydride. The mixture was stirred at room temperature overnight. After aqueous work-up (ether) and purification by PTLC, the 4-methoxybenzyl ester of the title compound was obtained. The ester was then dissolved in excess formic acid. The mixture was stirred at room temperature for 3 hours. After concentration in vacuo and purification by PTLC, the title compound was obtained. MS (CI): m/z=423 (M+H).

EXAMPLE 27

[1R-(1α,3aβ,4β,4aβ,7β,7aα,8aβ)]8a-[(4-bromobenzyloxy)methyl)]-4-formyl-44a,5,6,7,7a,8,8a-octahydro-7-methyl-3-(1-methylethyl)-1,4-methano-s-indacene-3a(1H)-carboxylic Acid The procedure of Example 26 was followed, with the use of 4-bromobenzyl bromide instead of benzyl bromide. MS (CI): m/z=501, 503 (M+H).

EXAMPLE 28

[1R-(1α,3aβ,4β,4aβ,7β,7aα,8aβ)]8a-[(1-but-2-enyloxy)methyl)]-4-formyl-4,4a,5,6,7,7a,8,8a-octahydro-7-methyl-3-(1-methylethyl)-1,4-methano-s-indacene-3a(1H)-carboxylic Acid The procedure of Example 26 was followed, with the use of crotyl chloride instead of benzyl bromide. MS (CI): m/z=387 (M+H).

EXAMPLE 29

[1R-(1α,3aβ,4β,4aβ,7β,7aα,8aβ)]8a-[(1-pent-2-enyloxy)methyl)]-4-formyl-4,4a,5,6,7,7a,8,8a-octahydro-7-methyl-3-(1-methylethyl)-1,4-methano-s-indacene-3a(1H)-carboxylic Acid The procedure of Example 26 was followed, with the use of trans-1-bromo-2-pentene instead of benzyl bromide. MS (CI): m/z=401 (M+H).

EXAMPLE 30

[1R-(1α,3aβ,4β,4aβ,7β,7aα,8aβ)]8a-[(isobutenyloxy)methyl)]-4-formyl-4,4a,5,6,7,7a,8,8a-octahydro-7-methyl-3-(1-methylethyl)-1,4-methano-s-indacene-3a(1H)-carboxylic Acid The procedure of Example 26 was followed, with the use of 2-(bromomethyl)propene instead of benzyl bromide. MS (CI): m/z=387 (M+H).

EXAMPLES 31–36

Following the procedure of Example 3, the following esters were prepared:

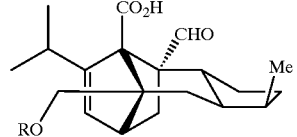

| Acylating Agent | Product (R) | Mass Spectrum (m/z) |
|---|---|---|
| CH$_3$(CH$_2$)$_2$COCl | CH$_3$(CH$_2$)$_2$CO— | 420.4 ((M + NH$_4$) |
| CH$_3$(CH$_2$)$_3$COCl | CH$_3$(CH$_2$)$_3$CO— | 434.4 (M + NH$_4$) |
| CH$_3$(CH$_2$)$_4$COCl | CH$_3$(CH$_2$)$_4$CO— | 448.5 (M + NH$_4$) |
| CH$_3$(CH$_2$)$_6$COCl | CH$_3$(CH$_2$)$_6$CO— | 476.5 (M + NH$_4$) |
| (CH$_3$)$_3$COCl | (CH$_3$)$_3$CO— | 434.3 (M + NH$_4$) |
| (CH$_3$)$_2$CHCH$_2$COCl | (CH$_3$)$_2$CHCH$_2$CO— | 434.4 (M + NH$_4$) |

EXAMPLES 37–46

Following the procedure of Example 3, the following esters may be prepared:

| Acylating Agent | Product (R) | MW |
|---|---|---|
| (CH$_3$)$_2$CHCOCl | (CH$_3$)$_2$CHCO— | 402.5296 |
| C$_6$H$_5$COCl | C$_6$H$_5$CO— | 436.5468 |
| m-CH$_3$C$_6$H$_4$COCl | m-CH$_3$C$_6$H$_4$CO— | 450.5736 |
| o-FC$_6$H$_4$COCl | o-FC$_6$H$_4$CO— | 454.5373 |
| C$_6$H$_5$CH$_2$COCl | C$_6$H$_5$CH$_2$CO— | 450.5736 |
| C$_6$H$_5$(CH$_2$)$_2$COCl | C$_6$H$_5$(CH$_2$)$_2$CO— | 464.6004 |
| 1-Naphthoyl Chloride | 1-Naphthoyl | 486.6066 |
| 2-Naphthoyl Chloride | 2-Naphthoyl | 486.6066 |
| 2-Pyrazinecarbonyl Chloride | 2-Pyrazinecarbonyl | 438.5224 |
| 2-Furoyl Chloride | 2-Furoyl | 426.5084 |

EXAMPLE 47

[1R-(1α,3aβ,4β,4aβ,7β,7aα,8aβ)]8a-[(2-pyridylcarboxy)methyl]-4-formyl-4,4a,5,6,7,7a,8,8a-octahydro-7-methyl-3-(1-methylethyl)-1,4-methano-s-indacene-3a(1H)-carboxylic Acid A solution of nicotinic acid (16 mg, 0.13 mmol) was prepared in 2 mL of dry dichloromethane. N,N-Dimethylamino-pyridine (2 mg, 0.01 mmol) was added followed by dicyclohexyl-carbodiimide (27 mg, 0.13 mmol). Sordaricin benzyl ester (50 mg, 0.118 mmol) was added and the mixture was stirred under an inert atmosphere for 24 h. The mixture was filtered and the organic layer was washed twice with water, twice with 5% acetic acid and again with water. The organic phase was dried over sodium sulfate, filtered and concentrated in vacuo. Purification by PTLC (2:1/hexanes:ethyl acetate) gave 41.5 mg (67%) of the benzyl ester of the title compound.

The purified product was dissolved in 2 mL of methanol and approximately 2 mg of palladium hydroxide on carbon was added. The reaction vessel was flushed with hydrogen gas and stirred vigorously at room temperature for one hour. The catalyst was removed by filtration through a celite pad and the filtrate was concentrated in vacuo to give the crude product. Purification by HPLC (C18 Zorbax, 40:60/95% water with 5% acetonitrile:95% acetonitrile with 5% water, 210 nm detection) gave 6.3 mg (18%) of the tide compound. Mass Spectrum (ESI): m/z=438.3 (M+H).

EXAMPLES 48–49

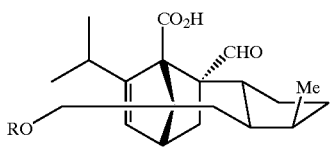

Following the procedure of Example 47 but substituting the appropriate carboxylic acid for nicotinic acid, the following compounds were prepared.

| Carboxylic Acid | Product (R) | Mass Spectrum (m/z) |
| --- | --- | --- |
| 2-pyridyl-CH$_2$-CO$_2$H | 2-pyridyl-CH$_2$-CH$_2$-CO— | 452.4 (M + H) |
| 2-quinolyl-CO$_2$H | 2-quinolyl-CH$_2$-CO— | 488.4 (M + H) |

EXAMPLES 50–52

To a CH$_2$Cl$_2$ solution of sordaricin p-methoxybenzyl ester (0.5 mg) is added NEt$_3$ (0.2 mL), followed by the appropriate acid chloride (10–100 mg). A catalytic amount of DMAP is added. The mixture is stirred at room temperature overnight. After purification by PTLC, the p-methoxybenzyl ester of the title compound is obtained. The ester is then dissolved in excess formic acid. The mixture is stirred at room temperature for 3 hours or a time sufficient to remove the protecting group. After concentration in vacuo and purification by PTLC, the title compound is obtained.

| Acylating Agent | Product (R) | MW |
| --- | --- | --- |
| CH$_2$=CH(CH$_2$)$_2$COCl | CH$_2$=CH(CH$_2$)$_2$CO— | 414.5406 |
| (CH$_3$)$_2$C=CHCOCl | (CH$_3$)$_2$C=CHCO— | 414.5406 |
| p-ClC$_6$H$_4$COCl | p-ClC$_6$H$_4$CO— | 470.9919 |

EXAMPLES 53–54 p-Methoxybenzylsordaricin ester was dissolved in dichloromethane and placed under an inert atmosphere of dry nitrogen. A slight molar excess of diisopropylethylamine was added and the mixture was cooled in a dry ice-acetone bath. A slight molar excess of acylating agent as described below was added and the mixture was stirred at −78° C. until a significant portion of the starting alcohol was consumed. The reaction was quenched, warmed to room temperature and concentrated in vacuo. Purification by PTLC gave the p-methoxybenzyl ester of the desired compound.

The compound obtained above was dissolved in formic acid and stirred at room temperature for 3 hours or a time sufficient to remove the p-methoxybenzyl ester. After concentration in vacuo and purification by PTLC, the desired compound as shown below was obtained.

| Acylating Agent | Product (R) | Mass Spectrum (m/z) |
| --- | --- | --- |
| H$_2$C=CHCOCl | H$_2$C=CHCO— | 404 (M + NH$_4$) |
| H$_3$CCH=CHCOCl | H$_3$CCH=CHCO— | 418 (M + NH$_4$) |

EXAMPLES 55–67

Following the procedure of that in Example 2, the following esters may be prepared:

| Acylating Agent | Product (R) | MW |
| --- | --- | --- |
| cyclohexane carboxylic acid | cyclohexane carbonyl | 442.5942 |
| cyclopentane carboxylic acid | cyclopentane carbonyl | 428.5674 |
| cyclobutane carboxylic acid | cyclobutane carbonyl | 414.5406 |
| p-CH$_3$C$_6$H$_4$CO$_2$H | p-CH$_3$C$_6$H$_4$CO— | 450.5736 |
| m-FC$_6$H$_4$CO$_2$H | m-FC$_6$H$_4$CO— | 454.5373 |
| 4-biphenylcarboxylic acid | 4-biphenylcarbonyl | 512.6444 |
| 3-biphenylcarboxylic acid | 3-biphenylcarbonyl | 512.6444 |
| 4,4'-terphenylcarboxylic acid | 4,4'-terphenylcarbonyl | 588.7420 |
| 9-anthracenecarboxylic acid | 9-anthracenecarbonyl | 536.6664 |
| 2-pyrrolecarboxylic acid | 2-pyrrolecarbonyl | 425.5236 |
| (CH$_3$)$_2$CH(CH$_2$)$_2$CO$_2$H | (CH$_3$)$_2$CH(CH$_2$)$_2$CO— | 430.5832 |
| HCO$_2$H | HCO- | 360.4492 |
| 2-thiophenecarboxylic acid | 2-thiophenecarbonyl | 442.5690 |

EXAMPLES 68–70

To a THF solution of the acid (0.16 mmol) is added NEt$_3$ (34 μL), followed by 2,4,6-trichlorobenzoyl chloride (25 μL). The mixture is stirred at room temperature for 15 minutes. Sordarin p-methoxybenzyl ester (1.0 mg) in 1 mL of THF is then added to this mixture, followed by the addition of DMAP (20 mg). This mixture is stirred at room temperature for 1 hour. After purification by PTLC, the p-methoxybenzyl ester of the desired compound is obtained. The ester is then dissolved in excess formic acid. The mixture is stirred at room temperature for 3 hours or a time sufficient to remove the protecting group. After concentration in vacuo and purification by PTLC, the desired compound is obtained.

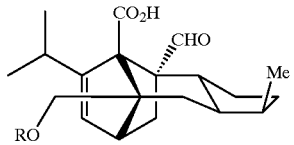

| Acylating Agent | Product (R) | MW |
|---|---|---|
| o-ClC$_6$H$_4$CO$_2$H | o-ClC$_6$H$_4$CO— | 470.9919 |
| 3,5-dibromobenzoic acid | 3,5-dibromobenzoyl | 594.3390 |
| cyclopropane carboxylic acid | cyclopropylcarbonyl | 400.5138 |

EXAMPLES 71–81

In a manner analogous to that in Example 4, the following carbonates may be prepared:

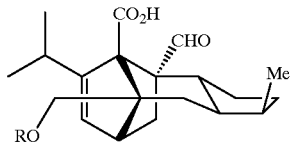

| Acylating Agent | Product (R) | MW |
|---|---|---|
| ethyl chloroformate | ethoxycarbonyl | 404.5022 |
| phenyl chloroformate | phenoxycarbonyl | 452.5462 |
| tert-butyl chloroformate | tert-butoxycarbonyl | 432.5558 |
| cyclopropyl chloroformate | cyclopropoxycarbonyl | 416.5132 |
| n-butyl chloroformate | n-butoxycarbonyl | 432.5558 |
| (CH$_3$)$_2$CHCH$_2$OCOCl | (CH$_3$)$_2$CHCH$_2$OCO— | 432.5558 |
| sec-butyl chloroformate | sec-butoxycarbonyl | 432.5558 |
| isopropyl chloroformate | isopropoxycarbonyl | 418.5290 |
| C$_6$H$_5$(CH$_2$)$_2$OCOCl | C$_6$H$_5$(CH$_2$)$_2$OCO— | 480.5998 |
| n-propyl chloroformate | n-propoxycarbonyl | 418.5290 |
| cyclohexylchloroformate | cyclohexoxycarbonyl | 458.5936 |

EXAMPLES 82–86

To a CH$_2$Cl$_2$ solution of sordaricin p-methoxybenzyl ester (0.5 mg) is added NEt$_3$ (0.2 mL), followed by the appropriate acid chloride (10–100 mg). A catalytic amount of DMAP is added. The mixture is stirred at room temperature overnight. After purification by PTLC, the p-methoxybenzyl ester of the title compound is obtained. The ester is then dissolved in excess formic acid. The mixture is stirred at room temperature for 0.25–3 hours or a time sufficient to remove the protecting group. After concentration in vacuo and purification by PTLC, the title compound is obtained.

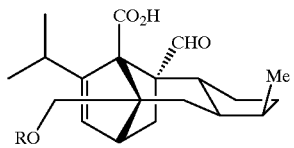

| Acylating Agent | Product (R) | MW |
|---|---|---|
| benzyl chloroformate | benzyloxycarbonyl | 466.5730 |
| p-methylbenzyl chloroformate | p-methylbenzyloxycarbonyl | 480.5998 |
| 1-naphthyl chloroformate | 1-naphthyloxycarbonyl | 516.6328 |
| 2-naphthalene chlorofomate | 2-naphthoxycarbonyl | 502.6060 |
| CH$_2$=CH(CH$_2$)$_2$OCOCl | CH$_2$=CH(CH$_2$)$_2$OCO— | 430.5400 |

EXAMPLES 87–88

Following the procedure of that in Examples 4, the following carbonates may be prepared:

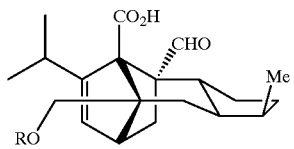

| Acylating Agent | Product (R) | MW |
|---|---|---|
| allyl chloroformate | allyloxycarbonyl | 416.5132 |
| crotyl chloroformate | crotyloxycarbonyl | 430.5400 |

EXAMPLES 89–103

In a manner analogous to that in Example 5, the following carbamates may be prepared:

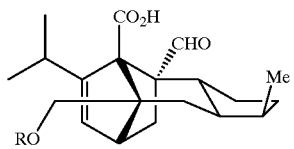

| Acylating Agent | Product (R) | MW |
|---|---|---|
| methyl isocyanate | methylaminocarbonyl | 389.4906 |
| phenyl isocyanate | anilinocarbonyl | 451.5614 |
| tert-butyl isocyanate | tert-butylaminocarbonyl | 431.5710 |
| cyclobutyl isocyanate | cyclobutylaminocarbonyl | 429.5552 |
| (CH$_3$)$_2$CHCH$_2$NCO | (CH$_3$)$_2$CHCH$_2$NHCO— | 431.5710 |
| p-CH$_3$C$_6$H$_4$NCO | p-CH$_3$C$_6$H$_4$NHCO | 465.5882 |
| isopropyl isocyanate | isopropylaminocarbonyl | 417.5442 |
| cyclopentyl isocyanate | cyclopentylaminocarbonyl | 443.5820 |
| naphthalene-1-isocyanate | 1-naphthylaminocarbonyl | 501.6212 |
| dimethylaminocarbonyl chloride | dimethylaminocarbonyl | 403.5174 |
| N-methyl-N-butylaminocabonyl chloride | N-methyl-N-butylaminocabonyl | 445.5978 |
| N-ethyl-N- | N-ethyl-N- | 403.5174 |

-continued

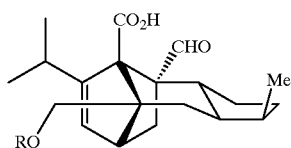

| Acylating Agent | Product (R) | MW |
|---|---|---|
| benzylaminocarbonyl chloride | benzylaminocarbonyl | |
| N-phenyl-N-2-naphthylaminocarbonyl chloride | N-phenyl-N-2-naphthylaminocabonyl | 577.7188 |
| N-methyl-N-phenylaminocarbonyl chloride | N-methyl-N-phenylaminocarbonyl | 465.5882 |
| N-methyl-N-cyclopropylaminocarbonyl chloride | N-methyl-N-cyclopropylaminocarbonyl | 429.5552 |

EXAMPLES 104–107

To a CHCl$_3$ solution of sordaricin p-methoxybenzyl ester (0.5 mg) is added the appropriate isocyanate (10–100 mg) and a catalytic amount of DMAP. The mixture is refluxed for 4 hours or until the reaction no longer proceeds. After concentration in vacuo and purification by PTLC, the p-methoxybenzyl ester of the desired compound is obtained. The ester is then dissolved in excess formic acid.

The mixture is stirred at room temperature for 3 hours or a time sufficient to remove the protecting group. After concentration in vacuo and purification by PTLC, the desired compound is obtained.

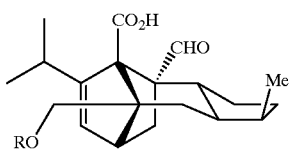

| Acylating Agent | Product (R) | MW |
|---|---|---|
| benzyl isocyanate | benzylaminocarbonyl | 465.5882 |
| allyl isocyanate | allylaminocarbonyl | 415.5284 |
| o-iodophenyl isocyanate | o-iodoanalinocarbonyl | 577.4580 |
| dibenzylaminocarbonyl chloride | dibenzylaminocarbonyl | 555.7126 |

EXAMPLE 108

[1R-(1α,3aβ,4β,4aβ,7β,7aα,8aβ)]8a-[((Z)-but-2-enyloxy)methyl]-4-formyl-4,4a,5,6,7,7a,8,8a-octahydro-7-methyl-3-(1-methylethyl)-1,4-methano-s-indacene-3a(1H)-carboxylic Acid Utilizing a procedure similar to that as described in Example 26, but using (Z)-1-p-toluenesulfonyloxy-2-butene in the place of benzyl bromide, the title compound was prepared. Partial $^1$H NMR (CDCl$_3$): δ 0.82 (3H, d), 0.98 (3H, d), 1.03 (3H, d), 3.24 (1H, d), 3.98 (1H, d), 4.04 (2H, d), 5.50 (1H, m), 5.76 (1H, m), 6.02 (1H, m), 9.89 (1H, s).

EXAMPLES 109–112

Following the procedure of Example 26, the following ethers were prepared:

| Alkylating Agent | Product (R-) | Mass Spectrum (m/z) |
|---|---|---|
| 1-p-toluenesulfonyloxy-2-butyne | H$_3$CC≡CCH$_2$— | 402.4 (M + NH$_4$) |
| 1-chloro-2-pentyne | CH$_3$CH$_2$C≡CCH$_2$— | 416.4 (M + NH$_4$) |
| (Z)-1-p-toluenesulfonyloxy-2-pentene | | 401.4 (M + H) |
| (Z)-1-p-toluenesulfonyloxy-2-hexene | | 415.4 (M + H) |

EXAMPLES 113–115

Following the procedure of Example 26, the following ethers may be prepared:

| Alkylating Agent | Product (R-) | MW |
|---|---|---|
| 1-bromo-2-propyne | HC≡CCH$_2$— | 370.4876 |
| 1-iodo-5-hexyne | HC≡CCH$_2$CH$_2$CH$_2$CH$_2$— | 412.5680 |
| cis-1-trimethylsilyloxy-4-bromo-2-butene | cis-4-hydroxy-2-butenyl | 402.5296 |

EXAMPLES 116–133

Following the procedure of Example 26, but substituting the appropriate alkylating agent for benzyl bromide, the following ethers were prepared:

| Alkylating Agent | Product (R-) | Mass Spectrum (m/z) |
|---|---|---|
| 3-methylbenzyl bromide | 3-methylbenzyl | 437 (M + H) |
| 4-methylbenzyl bromide | 4-methylbenzyl | 437 (M + H) |

-continued

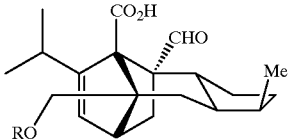

| Alkylating Agent | Product (R-) | Mass Spectrum (m/z) |
| --- | --- | --- |
| 2-methylbenzyl chloride | 2-methylbenzyl | 437 (M + H) |
| 2-fluorobenzyl bromide | 2-fluorobenzyl | 441 (M + H) |
| 3-fluorobenzyl bromide | 3-fluorobenzyl | 441 (M + H) |
| 4-fluorobenzyl bromide | 4-fluorobenzyl | 441 (M + H) |
| 3-methoxybenzyl bromide | 3-methoxybenzyl | 453 (M + H) |
| 1-naphthyl bromide | 1-naphthyl | 473 (M + H) |
| 2-phenylbenzyl bromide | 2-phenylbenzyl | 499 (M + H) |
| 2,3-difluorobenzyl bromide | 2,3-difluorobenzyl | 459 (M + H) |
| 2,4-difluorobenzyl bromide | 2,4-difluorobenzyl | 459 (M + H) |
| 2,5-difluorobenzyl bromide | 2,5-difluorobenzyl | 459 (M + H) |
| 2,6-difluorobenzyl bromide | 2,6-difluorobenzyl | 459 (M + H) |
| 3,5-difluorobenzyl bromide | 3,5-difluorobenzyl | 459 (M + H) |
| 3-carbomethoxybenzyl bromide | 3-carbomethoxybenzyl | 481 (M + H) |
| 1-(benzene-sulfonyloxymethyl)-3-cyclohexene | (3-cyclohexenyl)methyl | 427 (M + H) |
| 5-chloro-2-(chloromethyl)thiophene | (5-chloro-2-thienyl)methyl | 480 (M + NH$_4$) |
| 2,5-dimethyl-3-(chloromethyl)isoxazole | (2,5-dimethyl-3-isoxazolyl)methyl | 442 (M + H) |

EXAMPLE 134

[1R-(1α,3aβ,4β,4aβ,7β,7aα,8aβ)]8a-[(2-hydroxyethyloxy)methyl]-4-formyl-4,4a,5,6,7,7a,8,8a-octahydro-7-methyl-3-(1-methylethyl)-1,4-methano-s-indacene-3a(1H)-carboxylic Acid A solution of sordaricin benzyl ester (735.3 mg, 1.74 mmol) and 1-benzyloxy-2-benzenesulfonyloxyethane (3.94 g, 13.5 mmol) was prepared in 20 mL of N,N-dimethylformamide. Sodium hydride (210 mg of a 60% dispersion in mineral oil, 5.25 mmol) was added at room temperature and the mixture was stirred overnight. The reaction was quenched carefully with water and extracted with ether. Purification by flash chromatography gave 756 mg (78%) of benzyl [1R-(1α,3aβ,4β,4aβ,7β,7aα,8aβ)]8a-[(2-benzyloxyethyloxy)methyl]-4-formyl-4,4a,5,6,7,7a,8,8a-octahydro-7-methyl-3-(1-methylethyl)-1,4-methano-s-indacene-3a(1H)-carboxylic ester.

The product from above (700 mg, 1.26 mmol) was dissolved in 15 mL of methanol and 200 mg of palladium hydroxide on carbon (Pearlman's catalyst) was added. The mixture was stirred under one atmosphere of hydrogen gas for 30 minutes. The catalyst was removed by filtration and the filtrate was concentrated under reduced pressure to give the title compound. Mass spectrum (m/z): 377 (M+H).

EXAMPLE 135

[1R-(1α,3aβ,4β,4aβ,7β,7aα,8aβ)]8a-[(3-hydroxypropyloxy)methyl]-4-formyl-4,4a,5,6,7,7a,8,8a-octahydro-7-methyl-3-(1-methylethyl)-1,4-methano-s-indacene-3a(1H)-carboxylic Acid A solution of sordaricin benzyl ester (695 mg, 1.64 mmol) and 1-benzyloxy-3-benzenesulfonyloxypropane (5.04 g, 16.5 mmol) was prepared in 20 mL of N,N-dimethylformamide. Sodium hydride (200 mg of a 60% dispersion in mineral oil, 5.00 mmol) was added at room temperature and the mixture was stirred overnight. The reaction was quenched carefully with water and extracted with ether. Purification by flash chromatography gave 704 mg (75%) of benzyl [1R-(1α,3aβ,4β,4aβ,7β,7aα,8aβ)]8a-[(3-benzyloxypropyloxy)methyl]-4-formyl-4,4a,5,6,7,7a,8,8a-octahydro-7-methyl-3-(1-methylethyl)-1,4-methano-s-indacene-3a(1H)-carboxylic ester. $^1$H NMR (CDCl$_3$): δ.

The product from above (308.5 mg, 0.541 mmol) was dissolved in 10 mL of methanol and 100 mg of palladium hydroxide on carbon (Pearlman's catalyst) was added. The mixture was stirred under one atmosphere of hydrogen gas for 30 minutes. The catalyst was removed by filtration and the filtrate was concentrated under reduced pressure to give 211 mg (quantitative yield) of the title compound. Mass spectrum (m/z): 391 (M+H).

EXAMPLE 136

Benzyl [1R-(1α,3aβ,4β,4aβ,7β,7aα,8aβ)]8a-[(2-hydroxyethyloxy)methyl]-4-formyl-4,4a,5,6,7,7a,8,8a-octahydro-7-methyl-3-(1-methylethyl)-1,4-methano-s-indacene-3a(1H)-carboxylate The product from Example 134 was dissolved in 15 mL of dry N,N-dimethylformamide containing 1 g of sodium hydrogen carbonate and 1.5 mL of benzyl bromide. The mixture was stirred overnight and partitioned between water and ether. The organic phase was dried over anhydrous sodium sulfate and purified by flash chromatography to give 534 mg (91%) of the title compound.

EXAMPLE 137

Benzyl [1R-(1α,3aβ,4β,4aβ,7β,7aα,8aβ)]8a-[(3-hydroxypropyloxy)methyl]-4-formyl-4,4a,5,6,7,7a,8,8a-octahydro-7-methyl-3-(1-methylethyl)-1,4-methano-s-indacene-3a(1H)-carboxylate The product from Example 135 was dissolved in 10 mL of dry N,N-dimethylformamide and 1 g of sodium hydrogen carbonate and 1 mL of benzyl bromide were added. The mixture was stirred overnight at room temperature and partitioned between water and ether. The organic phase was dried over anhydrous sodium sulfate and purified by flash chromatography to give 233.7 mg (90%) of the title compound.

EXAMPLES 138–140

Benzyl [1R-(1α,3aβ,4β,4aβ,7β,7aα,8aβ)]8a-[(2-hydroxyethoxy)methyl]-4-formyl-4,4a,5,6,7,7a,8,8a-octahydro-7-methyl-3-(1-methylethyl)-1,4-methano-s-indacene-3a(1H)-carboxylate was dissolved in dry N,N-dimethylformamide and excess sodium hydride (60% dispersion in mineral oil) and excess alkylating agent as indicated below were added. The mixture was stirred until most of the starting alcohol compound was consumed as determined by thin layer chromatography. The reaction mixture was quenched carefully with water and partitioned between ether and water. The organic phase was dried over anhydrous sodium sulfate, filtered, the volatiles removed under reduced pressure and the residue purified by PTLC to obtain the desired benzyl ester product.

The benzyl ester product from above was dissolved in methanol and palladium hydroxide on carbon was added. The reaction mixture was stirred vigorously under one atmosphere of hydrogen for 30 minutes or until thin layer chromatography indicated the reaction to be complete. The catalyst was removed by filtration and the filtrate concentrated under reduced pressure to give the indicated product.

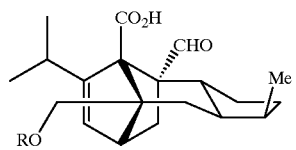

| Alkylating Agent | Product (R-) | Mass Spectrum (m/z) |
|---|---|---|
| iodoethane | $C_2H_5O(CH_2)_2$— | 405 (M + H) |
| n-butyl iodide | n-$C_4H_9O(CH_2)_2$— | 433 (M + H) |
| isobutenyl bromide | i-$C_4H_9O(CH_2)_2$— | 433 (M + H) |

EXAMPLES 141–146

Benzyl [1R-(1α,3aβ,4β,4aβ,7β,7aα,8aβ)]8a-[(3-hydroxypropyloxy)methyl]-4-formyl-4,4a,5,6,7,7a,8,8a-octahydro-7-methyl-3-(1-methylethyl)-1,4-methano-s-indacene-3a(1H)-carboxylate was dissolved in dry N,N-dimethylformamide and excess sodium hydride (60% dispersion in mineral oil) and excess alkylating agent as indicated below were added. The mixture was stirred until most of the starting alcohol compound was consumed as determined by thin layer chromatography. The reaction mixture was quenched carefully with water and partitioned between ether and water. The organic phase was dried over anhydrous sodium sulfate, filtered, the volatiles removed under reduced pressure and the residue purified by PTLC to obtain the desired benzyl ester product.

The benzyl ester product from above was dissolved in methanol and palladium hydroxide on carbon was added. The reaction mixture was stirred vigorously under one atmosphere of hydrogen for 30 minutes or until thin layer chromatography indicated the reaction to be complete. The catalyst was removed by filtration and the filtrate concentrated under reduced pressure to give the indicated product.

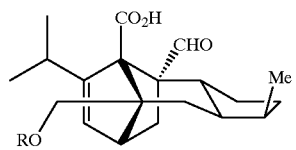

| Alkylating Agent | Product (R-) | Mass Spectrum (m/z) |
|---|---|---|
| iodomethane | $CH_3O(CH_2)_3$— | 405 (M + H) |
| iodoethane | $C_2H_5O(CH_2)_3$— | 419 (M + H) |
| allyl bromide | n-$C_3H_7O(CH_2)_3$— | 433 (M + H) |
| n-butyl iodide | n-$C_4H_9O(CH_2)_3$— | 447 (M + H) |
| n-pentyl iodide | n-$C_5H_{11}O(CH_2)_3$— | 461 (M + H) |
| 1-benzyloxy-3-benzenesulfonyloxypropane | $HO(CH_2)_3O(CH_2)_3$— | 466 (M + $NH_4$) |

EXAMPLE 147

Benzyl [1R-(1α,3aβ,4β,4aβ,7β,7aα,8aβ)]8a-[(3-hydroxypropyl)-3-oxypropyloxymethyl]-4-formyl-4, 4a,5,6,7,7a,8,8a-octahydro-7-methyl-3-(1-methylethyl)-1,4-methano-s-indacene-3a(1H)-carboxylate The product of Example 146 was dissolved in dry N,N-dimethylformamide and an excess of sodium hydrogen carbonate and an excess of benzyl bromide were added. The mixture was stirred overnight at room temperature and partitioned between water and ether. The organic phase was dried over anhydrous sodium sulfate and purified by flash chromatography to give the title compound.

EXAMPLES 148–152

Benzyl [1R-(1α,3aβ,4β,4aβ,7β,7aα,8aβ)]8a-[(3-hydroxypropyl)-3-oxypropyloxymethyl]-4-formyl-4,4a,5,6,7,7a,8,8a-octahydro-7-methyl-3-(1-methylethyl)-1,4-methano-s-indacene-3a(1H)-carboxylate was dissolved in dry N,N-dimethylformamide and excess sodium hydride (60% dispersion in mineral oil) and excess alkylating agent as indicated below were added. The mixture was stirred until most of the starting alcohol compound was consumed as determined by thin layer chromatography. The reaction mixture was quenched carefully with water and partitioned between ether and water. The organic phase was dried over anhydrous sodium sulfate, filtered, the volatiles removed under reduced pressure and the residue purified by PTLC to obtain the desired benzyl ester product.

The benzyl ester product from above was dissolved in methanol and palladium hydroxide on carbon was added. The reaction mixture was stirred vigorously under one atmosphere of hydrogen for 30 minutes or until thin layer chromatography indicated the reaction to be complete. The catalyst was removed by filtration and the filtrate concentrated under reduced pressure to give the indicated product.

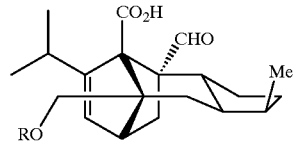

| Alkylating Agent | Product (R-) | Mass Spectrum (m/z) |
|---|---|---|
| iodomethane | $CH_3O(CH_2)_3O(CH_2)_3$— | 480 (M + $NH_4$) |
| iodoethane | $C_2H_5O(CH_2)_3O(CH_2)_3$— | 494 (M + $NH_4$) |
| allyl bromide | n-$C_3H_7O(CH_2)_3O(CH_2)_3$— | 508 (M + $NH_4$) |
| n-butyl iodide | n-$C_4H_9O(CH_2)_3O(CH_2)_3$— | 522 (M + $NH_4$) |
| n-pentyl iodide | n-$C_5H_{11}O(CH_2)_3O(CH_2)_3$— | 536 (M + $NH_4$) |

EXAMPLE 153

Benzyl [1R-(1α,3aβ,4β,4aβ,7β,7aα,8aβ)]8a-[(R-2-hydroxypropyloxy)methyl]-4-formyl-4,4a,5,6,7,7a,8, 8a-octahydro-7-methyl-3-(1-methylethyl)-1,4-methano-s-indacene-3a(1H)-carboxylate Sordaricin benzyl ester (450 mg, 1.07 mmol) and the benzenesulfonate of (S)-glycidol (approximately 3 g) were dissolved in 20 mL of dry N,N-dimethylformamide. Sodium hydride (128 mg of a 60% dispersion in mineral oil, 3.2 mmol) was added and the mixture was stirred at room temperature overnight. The reaction was carefully quenched with water and extracted with ether. The ether layer was dried with anhydrous sodium sulfate, filtered and concentrated under reduced pressure. Purification of the residue by flash chromatography gave 351.7 mg (69%) of benzyl [1R-(1α,3aβ,4β,4aβ,7β,7aα,8aβ)]8a-[(S-2,3-epoxypropyloxy)methyl]-4-formyl-4,4a,5,6,7,7a,8,8a-octahydro-7-methyl-3-(1-methylethyl)-1,4-methano-s-indacene-3a(1H)-carboxylate.

The product from above (340 mg, 0.711 mmol) was dissolved in 10 mL of methanol and 100 mg of palladium hydroxide on carbon (Pearlman's catalyst) was added. The mixture was stirred vigorously under one atmosphere of hydrogen for 30 minutes. The catalyst was removed by filtration and the filtrate was concentrated under reduced pressure.

The residue was dissolved in 15 mL of N,N-dimethylformamide and excess solid sodium hydrogen carbonate (0.5 g) and benzyl bromide (2 mL) were added. The mixture was stirred overnight and partitioned between ether and water. The organic phase was dried over anhydrous sodium sulfate, filtered and concentrated in vacuo. The residue was purified by flash chromatography to give 205 mg (61%) of the title compound. $^1$H NMR (CDCl$_3$): δ 0.51 (3H, d, J=7.1), 0.80 (3H, d, J=6.7), 1.00 (3H, d, J=6.8), 1.09 (3H, d, J=6.4), 0.80–2.30 (12H, m), 2.73 (1H, t, J=3.9), 3.08 (1H, dd, J=8.2, 9.6), 3.28 (1H, dd, J=3.0, 9.7), 3.47 (1H, d, J=8.9), 3.61 (1H, d, J=8.9), 3.88 (1H, m), 5.13 (1H, d, J=11.9), 5.22 (1H, d, J=11.9), 6.03 (1H, dd, J=1.3, 3.4), 7.28–7.38 (5H, m), 9.66 (1H, s).

EXAMPLES 154–158

Benzyl [1R-(1α,3aβ,4β,4aβ,7β,7aα,8aβ)]8a-[(R-2-hydroxypropyloxy)methyl]-4-formyl-4,4a,5,6,7,7a,8,8a-octahydro-7-methyl-3-(1-methylethyl)-1,4-methano-s-indacene-3a(1H)-carboxylate was dissolved in dry N,N-dimethylformamide and excess sodium hydride (60% dispersion in mineral oil) and excess alkylating agent as indicated below were added. The mixture was stirred until most of the starting alcohol compound was consumed as determined by thin layer chromatography. The reaction mixture was quenched carefully with water and partitioned between ether and water. The organic phase was dried over anhydrous sodium sulfate, filtered, the volatiles removed under reduced pressure and the residue purified by PTLC to obtain the desired benzyl ester product.

The benzyl ester product from above was dissolved in methanol and palladium hydroxide on carbon was added. The reaction mixture was stirred vigorously under one atmosphere of hydrogen for 30 minutes or until thin layer chromatography indicated the reaction to be complete. The catalyst was removed by filtration and the filtrate concentrated under reduced pressure to give the indicated product.

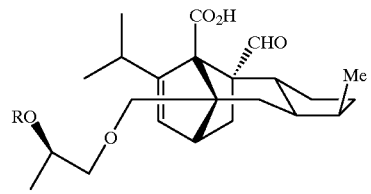

| Alkylating Agent | Product (R-) | Mass Spectrum (m/z) |
|---|---|---|
| iodomethane | CH$_3$— | 405 (M + H) |
| iodoethane | C$_2$H$_5$— | 419 (M + H) |
| allyl bromide | n-C$_3$H$_7$— | 450 (M + NH$_4$) |
| n-butyl iodide | n-C$_4$H$_9$— | 464 (M + NH$_4$) |
| n-pentyl iodide | n-C$_5$H$_{11}$— | 478 (M + NH$_4$) |

EXAMPLE 159

[1R-(1α,3aβ,4β,4aβ,7β,7aα,8aβ)]8a-[(m-carboxybenzyloxy)methyl]-4-formyl-4,4a,5,6,7,7a,8,8a-octahydro-7-methyl-3-(1-methylethyl)-1,4-methano-s-indacene-3a(1H)-carboxylic Acid The product of Example 130 was dissolved in methanol and aqueous sodium hydroxide was added and the mixture was stirred until starting material was consumed as determined by thin layer chromatographic analysis. The reaction was acidified and extracted with ethyl acetate to give the title compound. Mass spectrum (m/z): 467 (M+H).

EXAMPLE 160

[1R-(1α,3aβ,4β,4aβ,7β,7aα,8aβ)]8a-[(R-2-aminopropyloxy)methyl]-4-formyl-4,4a,5,6,7,7a,8,8a-octahydro-7-methyl-3-(1-methylethyl)-1,4-methano-s-indacene-3a(1H)-carboxylic Acid The compound of Example 16 was dissolved in N,N-dimethylformamide and excess benzyl bromide was added followed by excess solid sodium hydrogen carbonate. The reaction was stirred overnight. The mixture was concentrated in vacuo, chloroform was added and the mixture was filtered. Concentration under reduced pressure followed by purification of the residue by PTLC gave benzyl [1R-(1α,3aβ,4β,4aβ,7β,7aα,8aβ)]8a-[(R-2-hydroxypropyloxy)methyl]-4-formyl-4,4a,5,6,7,7a,8,8a-octahydro-7-methyl-3-(1-methylethyl)-1,4-methano-s-indacene-3a(1H)-carboxylate.

The benzyl ester from above was dissolved in dichloromethane and triethylamine was added followed by methanesulfonyl chloride. The reaction mixture was stirred for 30 minutes, concentrated in vacuo and the residue purified by PTLC to give benzyl [1R-(1α,3aβ,4β,4aβ,7β,7aα,8aβ)]8a-[(R-2-methanesulfonyloxypropyloxy)methyl]-4-formyl-4,4a,5,6,7,7a,8,8a-octahydro-7-methyl-3-(1-methylethyl)-1,4-methano-s-indacene-3a(1H)-carboxylate.

The methanesulfonate obtained above was dissolved in toluene and excess tetrabutylammonium azide in toluene was added. The mixture was heated to 70° C. until the starting material was consumed. After concentration in vacuo and purification by PTLC benzyl [1R-(1α,3aβ,4β,4aβ,7β,7aα,8aβ)]8a-[(S-2-azidopropyloxy)methyl]-4-formyl-4,4a,5,6,7,7a,8,8a-octahydro-7-methyl-3-(1-methylethyl)-1,4-methano-s-indacene-3a(1H)-carboxylate was obtained.

Benzyl [1R-(1α,3aβ,4β,4aβ,7β,7aα,8aβ)]8a-[( S-2-azidopropyloxy)methyl]-4-formyl-4,4a,5,6,7,7a,8,8a-octahydro-7-methyl-3-(1-methylethyl)-1,4-methano-s-indacene-3a(1H)-carboxylate was dissolved in methanol and palladium hydroxide on carbon was added. The mixture was stirred vigorously under one atmosphere of hydrogen for 30 minutes. The catalyst was removed by filtration and the filtrate was concentrated under reduced pressure to give the title compound. $^1$H NMR (CD$_3$OD): δ 0.82 (3H, m), 0.91 (3H, m), 0.93 (3H, m), 1.10 (3H, m), 1.10–2.40 (13H, m), 3.20–4.00 (5H, m), 5.87 (1H, m), 9.83 (1H, s).

EXAMPLE 161

[1R-(1α,3aβ,4β,4aβ,7β,7aα,8aβ)]8a-[(aminoacetyloxy)methyl]-4-formyl-4,4a,5,6,7,7a,8,8a-octahydro-7-methyl-3-(1-methylethyl)-1,4-methano-s-indacene-3a(1H)-carboxylic Acid Sordaricin benzyl ester and triethylamine were dissolved in dichloromethane and cooled to −78° C. Chloroacetyl chloride and N,N-dimethylaminopyridine were added and the mixture was stirred at −78° C. for 3 hours. The mixture was warmed to room temperature and after workup was purified by PTLC to give benzyl [1R-(1α,3aβ,4β,4aβ,7β,7aα,8aβ)]8a-[(chloroacetyloxy)methyl]-4-formyl-4,4a,5,6,7,7a,8,8a-octahydro-7-methyl-3-(1-methylethyl)-1,4-methano-s-indacene-3a(1H)-carboxylate.

The product from above was dissolved in toluene and excess tetrabutylammonium azide was added. The mixture was stirred overnight then concentrated in vacuo and the residue purified by PTLC to give benzyl [1R-(1α,3aβ,4β,4aβ,7β,7aα,8aβ)]8a-[(azidoacetyloxy)methyl]-4-formyl-4,4a,5,6,7,7a,8,8a-octahydro-7-methyl-3-(1-methylethyl)-1,4-methano-s-indacene-3a(1H)-carboxylate.

The azide obtained above was dissolved in methanol and palladium hydroxide on carbon was added. The reaction was stirred under one atmosphere of hydrogen for a time sufficient to remove the benzyl ester group and reduce the azide. Concentration under reduced pressure gave the title compound. $^1$H NMR (CD$_3$OD): δ 0.77 (3H, d, J=6.4), 0.93 (3H, d, J=6.7), 0.94 (3H, d, J=6.6), 1.50–2.30 (1 1H, m), 2.36 (1H, m), 2.51 (1H, m), 3.60–4.60 (4H, m), 5.90 (1H, s), 9.81 (1H, s).

EXAMPLE 162

[1R-(1α,3aβ,4β,4aβ,7β,7aα,8aβ)]8a-[(4-hydroxybutyloxy)methyl]-4-formyl-4,4a,5,6,7,7a,8,8a-octahydro-7-methyl-3-(1-methylethyl)-1,4-methano-s-indacene-3a(1H)-carboxylic Acid Sordaricin benzyl ester was dissolved in N,N-dimethylformamide followed by excess 1-bromo-4-tert-butyldimethylsilyloxybut-2-yne. An excess amount of sodium hydride (60% dispersion in mineral oil) was added and the mixture was stirred at room temperature overnight. The mixture was concentrated in vacuo and the residue purified by PTLC to give benzyl [1R-(1α,3aβ,4β,4aβ,7β,7aα,8aβ)]8a-[(4-tert-butyldimethylsilyloxybut-2-yn-1-yloxy)methyl]-4-formyl-4,4a,5,6,7,7a,8,8a-octahydro-7-methyl-3-(1-methylethyl)-1,4-methano-s-indacene-3a(1H)-carboxylate.

The product above was dissolved in dry tetrahydrofuran and an excess of tetrabutylammonium fluoride (1M in tetrahydrofuran) was added. The mixture was stirred for one hour after which time it was concentrated in vacuo. The residue was purified by PTLC to give benzyl [1R-(1α,3aβ, 4β,4aβ,7β,7aα,8aβ)]8a-[(4-hydroxybut-2-yn-1-yl-oxy)methyl]-4-formyl-4,4a,5,6,7,7a,8,8a-octahydro-7-methyl-3-(1-methylethyl)-1,4-methano-s-indacene-3a(1H)-carboxylate.

The alcohol obtained above was dissolved in methanol and palladium hydroxide on carbon (Pearlman's catalyst) was added. The reaction mixture was stirred under one atmosphere of hydrogen for 3 hours. The mixture was filtered and the filtrate was concentrated in vacuo to give the title compound. $^1$H NMR (CDCl$_3$): δ 0.82 (3H, d, J=6.9), 0.95 (3H, d, J=6.7), 1.02 (3H, d, J=6.8), 1.20–2.10 (15H, m), 2.33 (1H, m), 2.37 (1H, m), 3.26–4.00 (6H, m), 6.02 (1H, m), 9.88 (1H, s).

EXAMPLE 163

[1R-(1α,3aβ,4β,4aβ,7β,7aα,8aβ)]8a-[( 2-aminoethoxy)methyl]-4-formyl-4,4a,5,6,7,7a,8,8a-octahydro-7-methyl-3-(1-methylethyl)-1,4-methano-s-indacene-3a(1H)-carboxylic Acid In a manner analogous to that of Example 160 but using the compound of Example 134 in place of the compound of Example 16, the title compound was obtained. Mass spectrum (m/z): 376 (M+H).

EXAMPLE 164

[1R-(1α,3aβ,4β,4aβ,7β,7aα,8aβ)]8a-[(cyclopentylmethyloxy)methyl]-4-formyl-4,4a,5,6,7,7a,8,8a-octahydro-7-methyl-3-(1-methylethyl)-1,4-methano-s-indacene-3a(1H)-carboxylic Acid To an N,N-dimethylformamide (DMF) solution of sordaricin benzyl ester was added excess cyclopentylmethyl benzenesulfonate, followed by NaH (60% oil dispersion). The mixture was stirred at room temperature overnight. After concentration in vacuo and purification by PTLC, the benzyl ester of the title compound was obtained. This derivative was dissolved in methanol and palladium hydroxide on carbon (Pearlman's catalyst) was added. The mixture was stirred under hydrogen (balloon pressure) until removal of the benzyl group was complete as determined by TLC. After concentration in vacuo and purification by PTLC, the title compound was obtained. Mass spectrum (m/z): 415 (M+H).

What is claimed is:

1. A compound having the formula I:

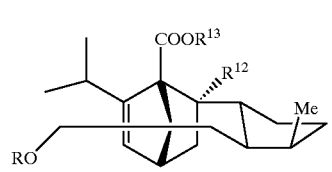

wherein

R is
  (a) C(=O)OR$^1$,
  (b) C(=O)NR$^2$R$^3$
  (c) C(=O)R$^4$,
  (d) CH(R$^2$)OR$^5$, (e) C(R$^6$)R$^7$)(R$^8$), (f) 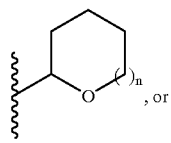, or (g) 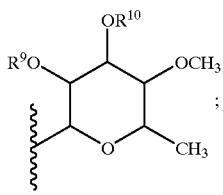;

with the proviso that when R$^{12}$ is CHO, R is not (g);

R$^1$ is
(a) C$_1$–C$_{14}$ alkyl,
(b) C$_2$–C$_{14}$ alkenyl,
(c) C$_2$–C$_{14}$ alkynyl,
(d) C$_3$–C$_{20}$ cycloalkyl,
(e) C$_3$–C$_{20}$ cycloalkenyl,
(f) aryl or
(g) aryl C$_{1-6}$ alkyl;

R$^2$ and R$^3$ are independently
(a) H or
(b) R$^1$;

R$^4$ is
(a) H,
(b) R$^1$ or
(c) —(CH$_2$)$_m$NR$^2$R$^3$;

R$^5$ is
(a) R$^1$ or
(b) —(CH$_2$)$_x$O(CH$_2$)$_y$H;

R$^6$ is
(a) H,
(b) R$^1$,
(c) —(CH$_2$)$_y$CHR$^{11}$(CH$_2$)$_z$H,
(d) —(CH$_2$)$_y$C≡C(CH$_2$)$_z$H,
(e) —(CH$_2$)$_y$C(R$^7$)=CH(CH$_2$)$_z$H,
(f) —(CH$_2$)$_y$C≡C(CH$_2$)$_m$R$^{11}$,
(g) —(CH$_2$)$_y$C(R$^7$)=CH(CH$_2$)$_m$R$^{11}$,

R$^7$ and R$^8$ are independently
(a) H, or
(b) C$_1$–C$_{14}$ alkyl;

R$^9$ and R$^{10}$ are independently
(a) H,
(a) C$_1$–C$_{14}$ alkyl,
(a) C$_2$–C$_{14}$ alkenyl,
(a) aryl C$_{1-6}$ alkyl;

R$^{11}$ is (a) OR$^7$,
(b) OCH$_2$CH$_2$(CH$_2$)$_n$OR$^7$, or
(c) NR$^2$R$^3$;

R$^{12}$ is
(a) —C(=O)R$^{14}$,
(b) —CH=NOH, or
(c) —CH$_2$OCH$_3$;

R$^{13}$ is
(a) H,
(b) —CH$_2$C$_6$H$_5$, (c) —CH$_2$CH=CH$_2$, (d) 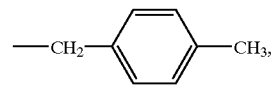

(e) 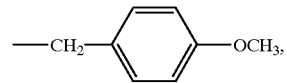

(f) 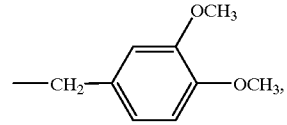

(g) 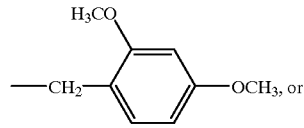, or (h) 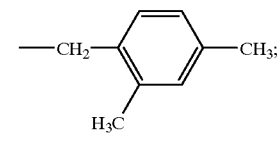;

R$^{14}$ is
(a) H,
(b) C$_1$–C$_4$ alkyl,
(c) —CCl$_3$,
(d) —CBr$_3$,
(e) —CF$_3$, or
(f) OH;

n is 0 or 1;
m is 1–6;
x is 2–6;
y is 0–6;
z is 0–6 or
a pharmaceutically or agriculturally acceptable salt thereof.

2. A compound of claim 1 wherein
R$^{12}$ is —CHO;
R is
(a) C(=O)OR$^1$,
(b) C(=O)NR$^2$R$^3$,
(c) C(=O)R$^4$,
(d) CH$_2$OR$^5$,
(e) C(R$^6$)R$^7$)(R$^8$), (f) 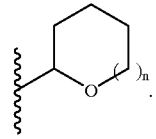.

3. A compound of claim 1 wherein
R$^{12}$ is —CHO
R$^{13}$ is H,
R is C(=O)OR$^1$.

4. A compound of claim 1 wherein $R^{12}$ is —CHO
$R^{13}$ is H,
R is $C(=O)NR^2R^3$.

5. A compound of claim 1 wherein
$R^{12}$ is —CHO
$R^{13}$ is H,
R is $C(=O)R^4$.

6. A compound of claim 1 wherein
$R^{12}$ is —CHO
$R^{13}$ is H,
R is $C(R^2)OR^5$.

7. A compound of claim 1 wherein
$R^{12}$ is —CHO
$R^{13}$ is H,
R is $C(R^6)R^7)(R^8)$.

8. A compound of claim 1 wherein
$R^{12}$ is —CHO
$R^{13}$ is H;

R is

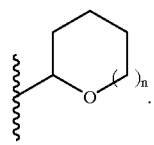

.

9. A compound of claim 1 wherein
$R^{12}$ is —CHO,
$R^{13}$ is H,
R is $CH(R^6)(R^7)$,
$R^6$ is
  (a) H,
  (b) $C_1$–$C_4$ alkyl,
  (c) aryl,
  (d) aryl $C_{1-6}$ alkyl,
  (e) —$(CH_2)_y CHR^{11} (CH_2)_z$,
  (f) —$(CH_2)_y C(R^7)=CH(CH_2)_z H$,
$R^7$ is H or $C_1$–$C_6$ alkyl,
$R^{11}$ is OH.

10. A compound of claim 1 wherein
$R^{12}$ is —CHO
$R^{13}$ is H,
R is
  (a) —$CH_3$,
  (b) —$CH_2CH_3$,
  (c) —$CH_2CH_2CH_3$,
  (d) —$CH_2CH_2CH_2CH_3$,
  (e) —$CH_2CH_2CH_2CH_2CH_3$,
  (f) —$CH_2CH_2CH_2CH_2CH_2CH_3$,
  (g) $CH_2CH_2CH_2CH_2CH_2CH_2CH_3$,
  (h) —$CH(CH_3)_2$,
  (i) —$CH_2CH(CH_3)_2$,
  (j) —$CH_2CH_2CH(CH_3)_2$,
  (k) —$CH_2C_6H_5$,
  (l) —$CH_2CH=CHCH_3$,
  (m) —$CH_2CH=CHCH_2CH_3$,
  (n) —$CH_2CH=CHCH_2CH_2CH_3$,
  (o) —$CH_2CH=CHCH_2CH_2CH_2CH_3$.

11. A compound of claim 1 wherein
$R^{12}$ is —CHO
$R^{13}$ is (a) H,
R is
  (a) —$CH_2CH_2CH_3$,
  (b) —$CH_2CH_2CH_2CH_3$,
  (c) —$CH_2CH_2CH_2CH_2CH_3$,
  (d) —$CH_2CH(CH_3)_2$,
  (e) —$CH_2CH_2CH(CH_3)_2$,
  (f) (Z)—$CH_2CH=CHCH_2CH_3$,
  (g) (Z)—$CH_2CH=CHCH_2CH_2CH_3$.

12. A pharmaceutical composition which comprises a compound of claim 1 and a pharmaceutically acceptable carrier.

13. An agrochemical composition which comprises a compound of claim 1 and a agriculturally acceptable carrier.

14. A method for the treatment or prevention of fungal infection in an animal which comprises administering to said animal an antifungal effective amount of a compound of claim 1.

15. A method for controlling phytopathogenic fungi which comprises administering to a plant in need of such control an antifungal effective amount of a compound of claim 1.

* * * * *